United States Patent
Zhang et al.

(10) Patent No.: US 12,133,765 B2
(45) Date of Patent: Nov. 5, 2024

(54) SYSTEMS AND METHODS FOR REAL-TIME TRACKING OF A TARGET TISSUE USING IMAGING BEFORE AND DURING THERAPY DELIVERY

(71) Applicant: Otsuka Medical Devices Co., Ltd., Tokyo (JP)

(72) Inventors: Jimin Zhang, Bellevue, WA (US); Shayin Jing, Seattle, WA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 797 days.

(21) Appl. No.: 17/171,940

(22) Filed: Feb. 9, 2021

(65) Prior Publication Data
US 2021/0161509 A1    Jun. 3, 2021

Related U.S. Application Data

(62) Division of application No. 14/929,056, filed on Oct. 30, 2015, now Pat. No. 10,925,579.
(Continued)

(51) Int. Cl.
*A61B 8/00* (2006.01)
*A61B 8/08* (2006.01)
(Continued)

(52) U.S. Cl.
CPC .............. *A61B 8/4254* (2013.01); *A61B 8/08* (2013.01); *A61B 8/085* (2013.01); *A61B 8/4263* (2013.01);
(Continued)

(58) Field of Classification Search
CPC ....... A61B 8/4254; A61B 8/5223; A61B 8/06; A61B 8/4488; A61B 8/488;
(Continued)

(56) References Cited

U.S. PATENT DOCUMENTS

| | | |
|---|---|---|
| 385,256 A | 6/1888 | Eggers |
| 3,274,437 A | 9/1966 | Mastrup |

(Continued)

FOREIGN PATENT DOCUMENTS

| | | |
|---|---|---|
| EP | 0225120 A2 | 6/1987 |
| EP | 0420758 A1 | 4/1991 |

(Continued)

OTHER PUBLICATIONS

Berjano, E., et al., "A Cooled Intraesophageal Balloon to Prevent Thermal Injury during Endocardial Surgical Radiofrequency Ablation of the left Atrium: a finite element study." Physics in Medicine and Biology, 50(20): 269-279, 2015.
(Continued)

*Primary Examiner* — Baisakhi Roy
(74) *Attorney, Agent, or Firm* — Theresa Ann Raymer

(57) ABSTRACT

Described herein are systems and methods for tracking a target tissue during therapy delivery. A system for identifying an anatomical structure and tracking the motion of the anatomical structure using imaging before and during delivery of a therapy to a patient includes an imaging module and a therapy module. In some cases, the imaging module is configured to identify a region of the anatomical structure in an image, and the therapy module is configured to deliver the therapy to a target tissue. A method for imaging during delivery of a therapy includes acquiring an image, identifying a region of an anatomical structure, tracking the region of the anatomical structure, integrating the tracking, generating a unique template library, determining if a pre-existing template matches the results or if the results should be updated as a new template, and delivering the therapy to the target tissue.

29 Claims, 13 Drawing Sheets

Related U.S. Application Data

(60) Provisional application No. 62/075,487, filed on Nov. 5, 2014.

(51) Int. Cl.

| | | |
|---|---|---|
| *A61B 17/225* | (2006.01) | |
| *A61N 7/02* | (2006.01) | |
| *G06T 7/246* | (2017.01) | |
| *G06T 7/44* | (2017.01) | |
| *A61B 8/06* | (2006.01) | |
| *A61B 17/00* | (2006.01) | |
| *A61B 18/00* | (2006.01) | |
| *A61B 18/20* | (2006.01) | |
| *A61B 34/20* | (2016.01) | |
| *A61B 90/00* | (2016.01) | |
| *A61N 5/10* | (2006.01) | |
| *A61N 7/00* | (2006.01) | |

(52) U.S. Cl.
CPC .......... *A61B 8/5207* (2013.01); *A61B 8/5223* (2013.01); *A61B 17/2256* (2013.01); *A61N 7/02* (2013.01); *G06T 7/246* (2017.01); *G06T 7/248* (2017.01); *G06T 7/44* (2017.01); *A61B 8/06* (2013.01); *A61B 8/4488* (2013.01); *A61B 8/488* (2013.01); *A61B 2017/00699* (2013.01); *A61B 2017/00703* (2013.01); *A61B 2018/00511* (2013.01); *A61B 18/20* (2013.01); *A61B 2034/2051* (2016.02); *A61B 2034/2065* (2016.02); *A61B 2090/378* (2016.02); *A61N 2005/1058* (2013.01); *A61N 2007/003* (2013.01); *A61N 2007/0052* (2013.01); *A61N 2007/0091* (2013.01); *A61N 2007/0095* (2013.01); *G06T 2207/30084* (2013.01)

(58) Field of Classification Search
CPC ...... A61N 2007/003; A61N 2007/0052; A61N 2007/0091
See application file for complete search history.

(56) References Cited

U.S. PATENT DOCUMENTS

| | | | |
|---|---|---|---|
| 3,499,437 A | 3/1970 | Balamuth et al. |
| 3,552,382 A | 1/1971 | Mount |
| 3,599,477 A | 8/1971 | Cohen et al. |
| 3,847,016 A | 11/1974 | Ziedonis |
| 3,927,662 A | 12/1975 | Ziedonis |
| 3,969,578 A | 7/1976 | Mezrich et al. |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pedersen |
| 4,237,901 A | 12/1980 | Taenzer |
| 4,273,127 A | 6/1981 | Auth et al. |
| 4,469,099 A | 9/1984 | McEwen |
| 4,479,494 A | 10/1984 | McEwen |
| 4,484,569 A | 11/1984 | Driller et al. |
| 4,545,386 A | 10/1985 | Hetz et al. |
| 4,601,296 A | 7/1986 | Yerushalmi |
| 4,605,010 A | 8/1986 | McEwen |
| 4,643,186 A | 2/1987 | Rosen |
| 4,650,466 A | 3/1987 | Luther |
| 4,688,578 A | 8/1987 | Takano et al. |
| 4,702,732 A | 10/1987 | Powers et al. |
| 4,708,836 A | 11/1987 | Gain et al. |
| 4,709,698 A | 12/1987 | Johnston et al. |
| 4,748,985 A | 6/1988 | Nagasaki |
| 4,757,820 A | 7/1988 | Itoh |
| 4,770,175 A | 9/1988 | McEwen |
| 4,773,865 A | 9/1988 | Baldwin |
| 4,773,899 A | 9/1988 | Spears |
| 4,784,148 A | 11/1988 | Dow et al. |
| 4,841,977 A | 6/1989 | Griffith et al. |
| 4,841,979 A | 6/1989 | Dow et al. |
| 4,850,363 A | 7/1989 | Yanagawa |
| 4,858,613 A | 8/1989 | Fry et al. |
| 4,905,672 A | 3/1990 | Schwarze et al. |
| 4,913,155 A | 4/1990 | Dow et al. |
| 4,929,246 A | 5/1990 | Sinofsky |
| 4,931,047 A | 6/1990 | Broadwin et al. |
| 4,938,216 A | 7/1990 | Lele |
| 4,938,217 A | 7/1990 | Lele |
| 4,955,377 A | 9/1990 | Lennox et al. |
| 4,957,099 A | 9/1990 | Hassler |
| 4,957,481 A | 9/1990 | Gatenby |
| 4,983,169 A | 1/1991 | Furukawa |
| 5,000,185 A | 3/1991 | Yock |
| 5,005,579 A | 4/1991 | Wurster et al. |
| RE33,590 E | 5/1991 | Dory |
| 5,026,387 A | 6/1991 | Thomas |
| 5,036,855 A | 8/1991 | Fry et al. |
| 5,039,774 A | 8/1991 | Shikinami et al. |
| 5,042,486 A | 8/1991 | Pfeiler et al. |
| 5,048,527 A | 9/1991 | Okazaki |
| 5,065,742 A | 11/1991 | Belikan et al. |
| 5,080,101 A | 1/1992 | Dory |
| 5,080,102 A | 1/1992 | Dory |
| 5,093,570 A | 3/1992 | Dorfi et al. |
| 5,114,423 A | 5/1992 | Kasprzyk |
| 5,150,712 A | 9/1992 | Dory |
| 5,170,790 A | 12/1992 | Lacoste et al. |
| 5,178,135 A | 1/1993 | Uchiyama et al. |
| 5,178,148 A | 1/1993 | Lacoste et al. |
| 5,181,522 A | 1/1993 | McEwen |
| 5,193,527 A | 3/1993 | Schafer |
| 5,194,291 A | 3/1993 | D'Aoust et al. |
| 5,211,160 A | 5/1993 | Talish et al. |
| 5,215,680 A | 6/1993 | D'Arrigo |
| 5,219,401 A | 6/1993 | Cathignol et al. |
| 5,230,334 A | 7/1993 | Klopotek |
| 5,230,921 A | 7/1993 | Waltonen et al. |
| 5,233,994 A | 8/1993 | Shmulewitz |
| 5,243,988 A | 9/1993 | Sieben et al. |
| 5,254,087 A | 10/1993 | McEwen |
| 5,263,957 A | 11/1993 | Davison |
| 5,290,278 A | 3/1994 | Anderson |
| 5,311,869 A | 5/1994 | Okazaki |
| 5,312,431 A | 5/1994 | McEwen |
| 5,352,195 A | 10/1994 | McEwen |
| 5,364,389 A | 11/1994 | Anderson |
| 5,368,591 A | 11/1994 | Lennox |
| 5,383,896 A | 1/1995 | Gershony et al. |
| 5,391,140 A | 2/1995 | Schaetzle et al. |
| 5,391,197 A | 2/1995 | Burdette et al. |
| 5,394,875 A | 3/1995 | Lewis et al. |
| 5,394,877 A | 3/1995 | Orr et al. |
| 5,413,550 A | 5/1995 | Castel |
| 5,415,657 A | 5/1995 | Taymor-Luria |
| 5,423,811 A | 6/1995 | Imran et al. |
| 5,439,477 A | 8/1995 | McEwen |
| 5,445,608 A | 8/1995 | Chen et al. |
| 5,453,576 A | 9/1995 | Krivitski |
| 5,454,373 A | 10/1995 | Koger et al. |
| 5,454,831 A | 10/1995 | McEwen |
| 5,471,988 A | 12/1995 | Fujio et al. |
| 5,474,071 A | 12/1995 | Chapelon et al. |
| 5,479,375 A | 12/1995 | Gualtieri |
| 5,492,126 A | 2/1996 | Hennige et al. |
| 5,501,655 A | 3/1996 | Rolt et al. |
| 5,503,152 A | 4/1996 | Oakley et al. |
| 5,507,744 A | 4/1996 | Tay et al. |
| 5,507,790 A | 4/1996 | Weiss |
| 5,515,853 A | 5/1996 | Smith et al. |
| 5,520,188 A | 5/1996 | Hennige et al. |
| 5,522,878 A | 6/1996 | Montecalvo et al. |
| 5,524,620 A | 6/1996 | Rosenschein |
| 5,526,815 A | 6/1996 | Granz et al. |
| 5,534,232 A | 7/1996 | Denes et al. |
| 5,536,489 A | 7/1996 | Lohrmann et al. |
| 5,553,618 A | 9/1996 | Suzuki et al. |

(56) References Cited

U.S. PATENT DOCUMENTS

| | | |
|---|---|---|
| 5,556,415 A | 9/1996 | McEwen et al. |
| 5,558,092 A | 9/1996 | Unger et al. |
| 5,558,672 A | 9/1996 | Edwards et al. |
| 5,573,497 A | 11/1996 | Chapelon |
| 5,574,212 A | 11/1996 | Madsen et al. |
| 5,575,788 A | 11/1996 | Baker et al. |
| 5,578,055 A | 11/1996 | McEwen |
| 5,584,853 A | 12/1996 | McEwen |
| 5,598,845 A | 2/1997 | Chandraratna et al. |
| 5,601,526 A | 2/1997 | Chapelon et al. |
| 5,607,447 A | 3/1997 | McEwen et al. |
| 5,609,485 A | 3/1997 | Bergman et al. |
| 5,626,601 A | 5/1997 | Gershony et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,657,755 A | 8/1997 | Desai |
| 5,657,760 A | 8/1997 | Ying et al. |
| 5,665,073 A | 9/1997 | Bulow et al. |
| 5,666,954 A | 9/1997 | Chapelon et al. |
| 5,681,339 A | 10/1997 | McEwen et al. |
| 5,685,307 A | 11/1997 | Holland et al. |
| 5,685,839 A | 11/1997 | Edwards et al. |
| 5,688,266 A | 11/1997 | Edwards et al. |
| 5,695,493 A | 12/1997 | Nakajima et al. |
| 5,697,897 A | 12/1997 | Buchholtz et al. |
| D389,574 S | 1/1998 | Emerson et al. |
| 5,711,058 A | 1/1998 | Frey |
| 5,716,374 A | 2/1998 | Francese et al. |
| 5,720,286 A | 2/1998 | Chapelon et al. |
| 5,720,287 A | 2/1998 | Chapelon et al. |
| 5,722,411 A | 3/1998 | Suzuki et al. |
| 5,726,066 A | 3/1998 | Choi |
| 5,735,796 A | 4/1998 | Granz et al. |
| 5,738,635 A | 4/1998 | Chapelon et al. |
| 5,741,295 A | 4/1998 | McEwen |
| 5,755,228 A | 5/1998 | Wilson et al. |
| 5,762,066 A | 6/1998 | Law et al. |
| 5,769,790 A | 6/1998 | Watkins et al. |
| 5,788,636 A | 8/1998 | Curley |
| 5,800,482 A | 9/1998 | Pomeranz et al. |
| 5,807,285 A | 9/1998 | Vaitekunas et al. |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos et al. |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,873,845 A | 2/1999 | Cline et al. |
| 5,879,314 A | 3/1999 | Peterson et al. |
| 5,882,302 A | 3/1999 | Driscoll, Jr. et al. |
| 5,882,328 A | 3/1999 | Levy et al. |
| 5,895,356 A | 4/1999 | Andrus et al. |
| 5,904,659 A | 5/1999 | Duarte et al. |
| 5,906,580 A | 5/1999 | Kline-Schoder et al. |
| 5,911,735 A | 6/1999 | McEwen et al. |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |
| 5,931,853 A | 8/1999 | McEwen et al. |
| 5,935,144 A | 8/1999 | Estabrook |
| 5,935,146 A | 8/1999 | McEwen et al. |
| 5,935,339 A | 8/1999 | Henderson et al. |
| 5,938,600 A | 8/1999 | Van Vaals et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A | 12/1999 | Martin et al. |
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |
| 6,039,694 A | 3/2000 | Larson et al. |
| 6,050,943 A | 4/2000 | Slayton et al. |
| 6,066,134 A | 5/2000 | Eggers et al. |
| 6,067,371 A | 5/2000 | Gouge et al. |
| 6,068,596 A | 5/2000 | Weth et al. |
| 6,071,239 A | 6/2000 | Cribbs et al. |
| 6,071,277 A | 6/2000 | Farley et al. |
| 6,078,831 A | 6/2000 | Belef et al. |
| 6,083,159 A | 7/2000 | Driscoll, Jr. et al. |
| 6,087,761 A | 7/2000 | Lorraine et al. |
| 6,097,985 A | 8/2000 | Kasevich et al. |
| 6,102,860 A | 8/2000 | Mooney |
| 6,106,463 A | 8/2000 | Wilk |
| 6,117,101 A | 9/2000 | Diederich et al. |
| 6,120,453 A | 9/2000 | Sharp |
| 6,128,522 A | 10/2000 | Acker et al. |
| 6,179,831 B1 | 1/2001 | Bliweis |
| 6,182,341 B1 | 2/2001 | Talbot et al. |
| 6,200,539 B1 | 3/2001 | Sherman et al. |
| 6,206,843 B1 | 3/2001 | Iger et al. |
| 6,213,939 B1 | 4/2001 | McEwen |
| 6,217,530 B1 | 4/2001 | Martin et al. |
| 6,221,015 B1 | 4/2001 | Yock |
| 6,231,507 B1 | 5/2001 | Zikorus et al. |
| 6,233,477 B1 | 5/2001 | Chia et al. |
| 6,246,156 B1 | 6/2001 | Takeuchi et al. |
| 6,254,598 B1 | 7/2001 | Edwards |
| 6,254,601 B1 | 7/2001 | Burbank et al. |
| 6,259,945 B1 | 7/2001 | Epstein et al. |
| 6,263,551 B1 | 7/2001 | Lorraine et al. |
| 6,267,734 B1 | 7/2001 | Ishibashi et al. |
| 6,270,458 B1 | 8/2001 | Barnea |
| 6,277,077 B1 | 8/2001 | Brisken et al. |
| 6,283,989 B1 | 9/2001 | Laufer et al. |
| 6,292,695 B1 | 9/2001 | Webster |
| 6,296,619 B1 | 10/2001 | Brisken et al. |
| 6,315,441 B2 | 11/2001 | King |
| 6,315,724 B1 | 11/2001 | Berman et al. |
| 6,332,089 B1 | 12/2001 | Acker et al. |
| 6,361,496 B1 | 3/2002 | Zikorus et al. |
| 6,361,548 B1 | 3/2002 | McEwen |
| 6,383,151 B1 | 5/2002 | Diederich et al. |
| 6,399,149 B1 | 6/2002 | Klett et al. |
| 6,406,759 B1 | 6/2002 | Roth |
| 6,409,720 B1 | 6/2002 | Hissong et al. |
| 6,419,669 B1 | 7/2002 | Frazier et al. |
| 6,425,867 B1 | 7/2002 | Vaezy et al. |
| 6,425,876 B1 | 7/2002 | Frangi et al. |
| 6,432,067 B1 | 8/2002 | Martin et al. |
| 6,443,894 B1 | 9/2002 | Sumanaweera et al. |
| 6,453,526 B2 | 9/2002 | Lorraine et al. |
| 6,488,639 B1 | 12/2002 | Ribault et al. |
| 6,491,672 B2 | 12/2002 | Slepian et al. |
| 6,494,848 B1 | 12/2002 | Sommercorn et al. |
| 6,500,133 B2 | 12/2002 | Martin et al. |
| 6,506,171 B1 | 1/2003 | Vitek et al. |
| 6,514,221 B2 | 2/2003 | Hynynen et al. |
| 6,514,249 B1 | 2/2003 | Maguire et al. |
| 6,520,915 B1 | 2/2003 | Lin et al. |
| 6,522,926 B1 | 2/2003 | Kieval et al. |
| 6,529,756 B1 | 3/2003 | Phan |
| 6,548,047 B1 | 4/2003 | Unger |
| 6,551,576 B1 | 4/2003 | Unger et al. |
| 6,559,644 B2 | 5/2003 | Froundlich et al. |
| 6,562,037 B2 | 5/2003 | Paton et al. |
| 6,565,557 B1 | 5/2003 | Sporri et al. |

(56) References Cited

U.S. PATENT DOCUMENTS

| | | |
|---|---|---|
| 6,576,168 B2 | 6/2003 | Hardcastle et al. |
| 6,584,360 B2 | 6/2003 | Francischelli et al. |
| 6,593,574 B2 | 7/2003 | Thomas et al. |
| 6,595,934 B1 | 7/2003 | Hissong et al. |
| 6,599,256 B1 | 7/2003 | Acker et al. |
| 6,599,288 B2 | 7/2003 | Maguire et al. |
| 6,602,251 B2 | 8/2003 | Burbank et al. |
| 6,612,988 B2 | 9/2003 | Maor et al. |
| 6,616,624 B1 | 9/2003 | Kieval |
| 6,626,855 B1 | 9/2003 | Weng et al. |
| 6,633,658 B1 | 10/2003 | Dabney et al. |
| 6,635,054 B2 | 10/2003 | Fjield et al. |
| 6,648,883 B2 | 11/2003 | Francischelli et al. |
| 6,652,461 B1 | 11/2003 | Levkovitz |
| 6,656,131 B2 | 12/2003 | Alster et al. |
| 6,656,136 B1 | 12/2003 | Weng et al. |
| 6,669,655 B1 | 12/2003 | Acker |
| 6,676,601 B1 | 1/2004 | Lacoste et al. |
| 6,682,483 B1 | 1/2004 | Abend et al. |
| 6,685,639 B1 | 2/2004 | Wang et al. |
| 6,692,490 B1 | 2/2004 | Edwards |
| 6,706,892 B1 | 3/2004 | Ezrin et al. |
| 6,709,392 B1 | 3/2004 | Salgo et al. |
| 6,709,407 B2 | 3/2004 | Fatemi |
| 6,716,184 B2 | 4/2004 | Vaezy et al. |
| 6,719,694 B2 | 4/2004 | Weng et al. |
| 6,719,699 B2 | 4/2004 | Smith |
| 6,719,755 B2 | 4/2004 | Sliwa, Jr. et al. |
| 6,726,627 B1 | 4/2004 | Lizzi et al. |
| 6,728,566 B1 | 4/2004 | Subramanyan et al. |
| 6,735,461 B2 | 5/2004 | Vitek et al. |
| 6,755,789 B2 | 6/2004 | Stringer et al. |
| 6,763,722 B2 | 7/2004 | Fjeld et al. |
| 6,764,488 B1 | 7/2004 | Burbank et al. |
| 6,837,886 B2 | 1/2005 | Collins |
| 6,846,291 B2 | 1/2005 | Smith et al. |
| 6,875,176 B2 | 4/2005 | Mourad et al. |
| 6,875,420 B1 | 4/2005 | Quay |
| 6,905,498 B2 | 6/2005 | Hooven |
| 6,932,771 B2 | 8/2005 | Whitmore et al. |
| 6,954,977 B2 | 10/2005 | Maguire |
| 6,955,648 B2 | 10/2005 | Mozayeni et al. |
| 6,978,174 B2 | 12/2005 | Gelfand et al. |
| 7,022,077 B2 | 4/2006 | Mourad et al. |
| 7,052,463 B2 | 5/2006 | Peszynski et al. |
| 7,052,695 B2 | 5/2006 | Kalish |
| 7,063,666 B2 | 6/2006 | Weng et al. |
| 7,128,711 B2 | 10/2006 | Medan et al. |
| 7,149,564 B2 | 12/2006 | Vining et al. |
| 7,156,816 B2 | 1/2007 | Schwartz et al. |
| 7,162,303 B2 | 1/2007 | Levin et al. |
| 7,211,060 B1 | 5/2007 | Talish et al. |
| 7,260,250 B2 | 8/2007 | Summers et al. |
| 7,285,093 B2 | 10/2007 | Anisimov et al. |
| 7,371,231 B2 | 5/2008 | Rioux et al. |
| 7,374,538 B2 | 5/2008 | Nightingale et al. |
| 7,445,599 B2 | 11/2008 | Kelly et al. |
| 7,470,241 B2 | 12/2008 | Weng et al. |
| 7,499,748 B2 | 3/2009 | Moffitt et al. |
| 7,510,536 B2 | 3/2009 | Foley et al. |
| 7,530,958 B2 | 5/2009 | Slayton et al. |
| 7,534,209 B2 | 5/2009 | Abend et al. |
| 7,553,284 B2 | 6/2009 | Vaitekunas |
| 7,617,005 B2 | 11/2009 | Demarais et al. |
| 7,620,451 B2 | 11/2009 | Demarais et al. |
| 7,621,873 B2 | 11/2009 | Owen et al. |
| 7,628,764 B2 | 12/2009 | Duarte et al. |
| 7,653,438 B2 | 1/2010 | Deem et al. |
| 7,684,865 B2 | 3/2010 | Aldrich et al. |
| 7,697,972 B2 | 4/2010 | Verard et al. |
| 7,698,947 B2 | 4/2010 | Sarr |
| 7,717,948 B2 | 5/2010 | Demarais et al. |
| 7,725,184 B2 | 5/2010 | Cazares |
| 7,766,833 B2 | 8/2010 | Lee et al. |
| 7,783,358 B2 | 8/2010 | Aldrich et al. |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,137,274 B2 | 3/2012 | Weng et al. |
| 8,295,912 B2 | 10/2012 | Gertner |
| 8,347,891 B2 | 1/2013 | Demarais et al. |
| 8,383,671 B1 | 2/2013 | Consigny |
| 8,447,414 B2 | 5/2013 | Johnson et al. |
| 8,483,831 B1 | 7/2013 | Hlavka et al. |
| 8,556,834 B2 | 10/2013 | Gertner |
| 8,626,300 B2 | 1/2014 | Demarais et al. |
| 8,702,619 B2 | 4/2014 | Wang |
| 8,715,209 B2 | 5/2014 | Gertner |
| 8,774,913 B2 | 7/2014 | Demarais et al. |
| 8,790,281 B2 | 7/2014 | Diederich et al. |
| 8,818,514 B2 | 8/2014 | Zarins et al. |
| 8,845,629 B2 | 9/2014 | Demarais et al. |
| 8,932,289 B2 | 1/2015 | Mayse et al. |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 11/2015 | Demarais et al. |
| 9,186,212 B2 | 11/2015 | Nabulovsky et al. |
| 9,234,878 B2 | 1/2016 | Lavrentyev et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 9,427,579 B2 | 8/2016 | Fain et al. |
| 9,439,598 B2 | 9/2016 | Shimada et al. |
| 9,649,064 B2 | 5/2017 | Toth et al. |
| 9,700,372 B2 | 7/2017 | Schaer |
| 9,707,034 B2 | 7/2017 | Schaer |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,230,041 B2 | 3/2019 | Taylor et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,350,440 B2 | 7/2019 | Taylor et al. |
| 10,363,359 B2 | 7/2019 | Toth et al. |
| 10,368,775 B2 | 8/2019 | Hettrick et al. |
| 10,368,944 B2 | 8/2019 | Schaer |
| 10,376,310 B2 | 8/2019 | Fain et al. |
| 10,383,685 B2 | 8/2019 | Gross et al. |
| 10,398,332 B2 | 9/2019 | Min et al. |
| 10,456,605 B2 | 10/2019 | Taylor et al. |
| 10,470,684 B2 | 11/2019 | Toth et al. |
| 10,478,249 B2 | 11/2019 | Gross et al. |

(56) References Cited

U.S. PATENT DOCUMENTS

| | | |
|---|---|---|
| 10,499,937 B2 | 12/2019 | Warnking |
| 10,543,037 B2 | 1/2020 | Shah |
| 10,850,091 B2 | 12/2020 | Zarins et al. |
| 11,801,085 B2 | 10/2023 | Wu et al. |
| 2001/0014775 A1 | 8/2001 | Koger et al. |
| 2001/0014805 A1 | 8/2001 | Burbank et al. |
| 2001/0023365 A1 | 9/2001 | Medhkour et al. |
| 2001/0032382 A1 | 10/2001 | Lorraine et al. |
| 2001/0041910 A1 | 11/2001 | McEwen |
| 2001/0044636 A1 | 11/2001 | Pedros et al. |
| 2002/0042610 A1 | 4/2002 | Sliwa, Jr. et al. |
| 2002/0055736 A1 | 5/2002 | Horn et al. |
| 2002/0072672 A1 | 6/2002 | Roundhill et al. |
| 2002/0072741 A1 | 6/2002 | Sliwa, Jr. et al. |
| 2002/0095164 A1 | 7/2002 | Andreas et al. |
| 2002/0143275 A1 | 10/2002 | Sarvazyan et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2002/0193831 A1 | 12/2002 | Smith, III |
| 2003/0004439 A1 | 1/2003 | Pant et al. |
| 2003/0009194 A1 | 1/2003 | Saker et al. |
| 2003/0010124 A1 | 1/2003 | Bates |
| 2003/0018255 A1 | 1/2003 | Martin et al. |
| 2003/0028111 A1 | 2/2003 | Vaezy et al. |
| 2003/0036771 A1 | 2/2003 | McEwen et al. |
| 2003/0050665 A1 | 3/2003 | Ginn |
| 2003/0060737 A1 | 3/2003 | Brisken |
| 2003/0069569 A1 | 4/2003 | Burdette et al. |
| 2003/0074039 A1 | 4/2003 | Puskas |
| 2003/0114756 A1 | 6/2003 | Li |
| 2003/0120204 A1 | 6/2003 | Unger et al. |
| 2003/0125726 A1 | 7/2003 | Maguire et al. |
| 2003/0149366 A1 | 8/2003 | Stringer et al. |
| 2003/0153849 A1 | 8/2003 | Huckle et al. |
| 2003/0181963 A1 | 9/2003 | Pellegrino et al. |
| 2003/0187371 A1 | 10/2003 | Vortman et al. |
| 2003/0195420 A1 | 10/2003 | Mendlein et al. |
| 2003/0208101 A1 | 11/2003 | Cecchi |
| 2003/0216721 A1 | 11/2003 | Diederich et al. |
| 2003/0216792 A1 | 11/2003 | Levin et al. |
| 2003/0225331 A1 | 12/2003 | Diederich et al. |
| 2004/0002654 A1 | 1/2004 | Davidson et al. |
| 2004/0019349 A1 | 1/2004 | Fuimaono et al. |
| 2004/0030227 A1 | 2/2004 | Littrup et al. |
| 2004/0030268 A1 | 2/2004 | Weng et al. |
| 2004/0030269 A1 | 2/2004 | Horn et al. |
| 2004/0039280 A1 | 2/2004 | Wu et al. |
| 2004/0049105 A1 | 3/2004 | Crutchfield et al. |
| 2004/0054287 A1 | 3/2004 | Stephens |
| 2004/0054289 A1 | 3/2004 | Eberle et al. |
| 2004/0056200 A1 | 3/2004 | Rothenfusser et al. |
| 2004/0057492 A1 | 3/2004 | Vona et al. |
| 2004/0071664 A1 | 4/2004 | McHale et al. |
| 2004/0078034 A1 | 4/2004 | Acker et al. |
| 2004/0078219 A1 | 4/2004 | Kaylor et al. |
| 2004/0082859 A1 | 4/2004 | Schaer |
| 2004/0082978 A1 | 4/2004 | Harrison et al. |
| 2004/0089811 A1 | 5/2004 | Lewis et al. |
| 2004/0097805 A1* | 5/2004 | Verard .................. A61B 34/20 600/428 |
| 2004/0097819 A1 | 5/2004 | Duarte |
| 2004/0097840 A1 | 5/2004 | Holmer |
| 2004/0106880 A1 | 6/2004 | Weng et al. |
| 2004/0113524 A1 | 6/2004 | Baumgartner et al. |
| 2004/0122493 A1 | 6/2004 | Ishibashi et al. |
| 2004/0122494 A1 | 6/2004 | Eggers et al. |
| 2004/0127798 A1 | 7/2004 | Dala-Krishna et al. |
| 2004/0153126 A1 | 8/2004 | Okai |
| 2004/0158154 A1 | 8/2004 | Hanafy et al. |
| 2004/0181178 A1 | 9/2004 | Aldrich et al. |
| 2004/0210214 A1 | 10/2004 | Knowlton |
| 2004/0220167 A1 | 11/2004 | Samiy |
| 2004/0234453 A1 | 11/2004 | Smith |
| 2004/0242999 A1 | 12/2004 | Vitek et al. |
| 2004/0254620 A1 | 12/2004 | Lacoste et al. |
| 2004/0267252 A1 | 12/2004 | Washington et al. |
| 2005/0038339 A1 | 2/2005 | Chauhan et al. |
| 2005/0038340 A1 | 2/2005 | Vaezy et al. |
| 2005/0043625 A1 | 2/2005 | Oliver et al. |
| 2005/0046311 A1 | 3/2005 | Baumgartner et al. |
| 2005/0054955 A1 | 3/2005 | Lidgren |
| 2005/0065436 A1 | 3/2005 | Ho et al. |
| 2005/0070790 A1 | 3/2005 | Niwa et al. |
| 2005/0085793 A1 | 4/2005 | Glossop |
| 2005/0090104 A1 | 4/2005 | Yang et al. |
| 2005/0092091 A1 | 5/2005 | Greelish |
| 2005/0096538 A1 | 5/2005 | Chomas et al. |
| 2005/0096542 A1 | 5/2005 | Weng et al. |
| 2005/0119704 A1 | 6/2005 | Peters et al. |
| 2005/0149126 A1 | 7/2005 | Libbus |
| 2005/0154299 A1 | 7/2005 | Hoctor et al. |
| 2005/0159738 A1 | 7/2005 | Visram et al. |
| 2005/0165298 A1 | 7/2005 | Larson et al. |
| 2005/0182297 A1 | 8/2005 | Gravenstein et al. |
| 2005/0182319 A1 | 8/2005 | Glossop |
| 2005/0192638 A1 | 9/2005 | Gelfand et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0240102 A1 | 10/2005 | Rachlin et al. |
| 2005/0240103 A1 | 10/2005 | Byrd et al. |
| 2005/0240126 A1* | 10/2005 | Foley .................. A61B 8/06 601/2 |
| 2005/0240127 A1 | 10/2005 | Seip et al. |
| 2005/0240170 A1 | 10/2005 | Zhang et al. |
| 2005/0240241 A1 | 10/2005 | Yun et al. |
| 2005/0261672 A1 | 11/2005 | Deem et al. |
| 2005/0277853 A1 | 12/2005 | Mast et al. |
| 2005/0288730 A1 | 12/2005 | Deem et al. |
| 2006/0004417 A1 | 1/2006 | Rossing et al. |
| 2006/0025756 A1 | 2/2006 | Francischelli et al. |
| 2006/0041277 A1 | 2/2006 | Deem et al. |
| 2006/0052695 A1 | 3/2006 | Adam et al. |
| 2006/0052701 A1 | 3/2006 | Carter et al. |
| 2006/0058678 A1 | 3/2006 | Vitek et al. |
| 2006/0058707 A1 | 3/2006 | Barthe et al. |
| 2006/0058711 A1 | 3/2006 | Harhen et al. |
| 2006/0064081 A1 | 3/2006 | Rosinko |
| 2006/0082771 A1 | 4/2006 | Doerrmann et al. |
| 2006/0084966 A1 | 4/2006 | Maguire et al. |
| 2006/0118127 A1 | 6/2006 | Chinn |
| 2006/0122514 A1 | 6/2006 | Byrd et al. |
| 2006/0142827 A1 | 6/2006 | Willard et al. |
| 2006/0184069 A1 | 8/2006 | Vaitekunas |
| 2006/0217772 A1 | 9/2006 | Libbus et al. |
| 2006/0235286 A1 | 10/2006 | Stone et al. |
| 2006/0235300 A1 | 10/2006 | Weng et al. |
| 2006/0235303 A1 | 10/2006 | Vaezy et al. |
| 2006/0287681 A1 | 12/2006 | Yonce et al. |
| 2006/0293712 A1 | 12/2006 | Kieval et al. |
| 2007/0004984 A1 | 1/2007 | Crum et al. |
| 2007/0016113 A1 | 1/2007 | Buchholtz et al. |
| 2007/0016274 A1 | 1/2007 | Boveja et al. |
| 2007/0038115 A1 | 2/2007 | Quigley et al. |
| 2007/0055155 A1 | 3/2007 | Owen et al. |
| 2007/0055181 A1 | 3/2007 | Deem et al. |
| 2007/0060921 A1 | 3/2007 | Janssen et al. |
| 2007/0066957 A1 | 3/2007 | Demarais et al. |
| 2007/0106292 A1 | 5/2007 | Kaplan |
| 2007/0106339 A1 | 5/2007 | Errico et al. |
| 2007/0112327 A1 | 5/2007 | Yun et al. |
| 2007/0129720 A1 | 6/2007 | Demarais et al. |
| 2007/0129761 A1 | 6/2007 | Demarais et al. |
| 2007/0135875 A1 | 6/2007 | Demarais et al. |
| 2007/0142879 A1 | 6/2007 | Greenberg et al. |
| 2007/0149880 A1 | 6/2007 | Willis |
| 2007/0167806 A1 | 7/2007 | Wood et al. |
| 2007/0179379 A1 | 8/2007 | Weng et al. |
| 2007/0203527 A1 | 8/2007 | Ben-David et al. |
| 2007/0213616 A1 | 9/2007 | Anderson et al. |
| 2007/0233185 A1 | 10/2007 | Anderson et al. |

(56) References Cited

U.S. PATENT DOCUMENTS

| | | |
|---|---|---|
| 2007/0239000 A1 | 10/2007 | Emery et al. |
| 2007/0265687 A1 | 11/2007 | Deem et al. |
| 2007/0282407 A1 | 12/2007 | Demarais et al. |
| 2008/0030104 A1 | 2/2008 | Prus |
| 2008/0033292 A1 | 2/2008 | Shafran |
| 2008/0033420 A1 | 2/2008 | Nields et al. |
| 2008/0039746 A1 | 2/2008 | Hissong et al. |
| 2008/0045864 A1 | 2/2008 | Candy et al. |
| 2008/0045865 A1 | 2/2008 | Kislev |
| 2008/0046016 A1 | 2/2008 | Ben-David et al. |
| 2008/0047325 A1 | 2/2008 | Bartlett |
| 2008/0051767 A1 | 2/2008 | Rossing et al. |
| 2008/0058683 A1 | 3/2008 | Gifford et al. |
| 2008/0194954 A1 | 8/2008 | Unger et al. |
| 2008/0200806 A1 | 8/2008 | Liu et al. |
| 2008/0200815 A1 | 8/2008 | Van Der Steen et al. |
| 2008/0215031 A1 | 9/2008 | Belfort et al. |
| 2008/0234569 A1 | 9/2008 | Tidhar et al. |
| 2008/0255498 A1 | 10/2008 | Houle |
| 2008/0255642 A1 | 10/2008 | Zarins et al. |
| 2008/0261009 A1 | 10/2008 | Kawabata |
| 2008/0288017 A1 | 11/2008 | Kieval et al. |
| 2008/0312561 A1 | 12/2008 | Chauhan |
| 2008/0312562 A1 | 12/2008 | Routh et al. |
| 2008/0317204 A1 | 12/2008 | Sumanaweera et al. |
| 2008/0319375 A1 | 12/2008 | Hardy |
| 2009/0000382 A1 | 1/2009 | Sathish et al. |
| 2009/0012098 A1 | 1/2009 | Jordan et al. |
| 2009/0036948 A1 | 2/2009 | Levin et al. |
| 2009/0054770 A1 | 2/2009 | Daigle |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0088623 A1 | 4/2009 | Vortman et al. |
| 2009/0099627 A1 | 4/2009 | Molnar et al. |
| 2009/0112095 A1 | 4/2009 | Daigle |
| 2009/0112133 A1 | 4/2009 | Deisseroth et al. |
| 2009/0137873 A1 | 5/2009 | Mitsuhashi |
| 2009/0149782 A1 | 6/2009 | Cohen |
| 2009/0163982 A1 | 6/2009 | deCharms |
| 2009/0221908 A1 | 9/2009 | Glossop |
| 2009/0221939 A1 | 9/2009 | Demarais et al. |
| 2009/0234407 A1 | 9/2009 | Hastings et al. |
| 2009/0247911 A1 | 10/2009 | Novak et al. |
| 2009/0248005 A1 | 10/2009 | Rusin et al. |
| 2009/0264755 A1 | 10/2009 | Chen et al. |
| 2009/0306644 A1 | 12/2009 | Mayse et al. |
| 2009/0315978 A1 | 12/2009 | Wurmlin et al. |
| 2010/0010393 A1 | 1/2010 | Duffy et al. |
| 2010/0022921 A1 | 1/2010 | Seip et al. |
| 2010/0023088 A1 | 1/2010 | Stack et al. |
| 2010/0042020 A1 | 2/2010 | Ben-Ezra |
| 2010/0081971 A1 | 4/2010 | Allison |
| 2010/0092424 A1 | 4/2010 | Sanghvi et al. |
| 2010/0125269 A1 | 5/2010 | Emmons et al. |
| 2010/0128141 A1 | 5/2010 | Jang |
| 2010/0160781 A1 | 6/2010 | Carter et al. |
| 2010/0172567 A1* | 7/2010 | Prokoski ............... A61B 5/411 |
| | | 348/47 |
| 2010/0174188 A1 | 7/2010 | Wang et al. |
| 2010/0286522 A1 | 11/2010 | Beach et al. |
| 2011/0021913 A1 | 1/2011 | Weng et al. |
| 2011/0028867 A1 | 2/2011 | Choo et al. |
| 2011/0060255 A1 | 3/2011 | Chen |
| 2011/0092781 A1 | 4/2011 | Gertner |
| 2011/0092880 A1* | 4/2011 | Gertner ............... A61B 5/412 |
| | | 604/20 |
| 2011/0112400 A1 | 5/2011 | Emery et al. |
| 2011/0118723 A1 | 5/2011 | Turner et al. |
| 2011/0118805 A1 | 5/2011 | Wei et al. |
| 2011/0124976 A1 | 5/2011 | Sabczynski et al. |
| 2011/0125206 A1 | 5/2011 | Bornzin |
| 2011/0208096 A1 | 8/2011 | Demarais et al. |
| 2011/0234834 A1 | 9/2011 | Sugimoto |
| 2011/0251489 A1 | 10/2011 | Zhang et al. |
| 2011/0257523 A1 | 10/2011 | Hastings et al. |
| 2011/0257561 A1 | 10/2011 | Gertner et al. |
| 2011/0260965 A1 | 10/2011 | Kim et al. |
| 2011/0319765 A1 | 12/2011 | Gertner et al. |
| 2012/0004656 A1 | 1/2012 | Jackson et al. |
| 2012/0016239 A1 | 1/2012 | Barthe et al. |
| 2012/0065492 A1 | 3/2012 | Gertner et al. |
| 2012/0071757 A1* | 3/2012 | Salcudean ............ A61B 34/20 |
| | | 600/439 |
| 2012/0109018 A1 | 5/2012 | Gertner et al. |
| 2012/0123243 A1 | 5/2012 | Hastings |
| 2012/0265198 A1 | 10/2012 | Crow et al. |
| 2012/0296232 A1 | 11/2012 | Ng |
| 2013/0023897 A1 | 1/2013 | Wallace |
| 2013/0085489 A1 | 4/2013 | Fain et al. |
| 2013/0096550 A1 | 4/2013 | Hill |
| 2013/0116737 A1 | 5/2013 | Edwards et al. |
| 2013/0120552 A1 | 5/2013 | Yamanaka et al. |
| 2013/0123770 A1 | 5/2013 | Smith |
| 2013/0131743 A1 | 5/2013 | Yamasaki et al. |
| 2013/0150749 A1 | 6/2013 | McLean et al. |
| 2013/0165925 A1 | 6/2013 | Mathur et al. |
| 2013/0245429 A1 | 9/2013 | Zhang et al. |
| 2013/0261688 A1* | 10/2013 | Dong ............... A61N 1/36542 |
| | | 607/28 |
| 2013/0274614 A1 | 10/2013 | Shimada et al. |
| 2013/0289369 A1 | 10/2013 | Margolis |
| 2013/0289682 A1 | 10/2013 | Barman et al. |
| 2014/0005477 A1 | 1/2014 | Gupta et al. |
| 2014/0018788 A1 | 1/2014 | Engelman et al. |
| 2014/0043933 A1 | 2/2014 | Belevich et al. |
| 2014/0058294 A1 | 2/2014 | Gross et al. |
| 2014/0086684 A1 | 3/2014 | Sehr et al. |
| 2014/0163540 A1 | 6/2014 | Iyer et al. |
| 2014/0171782 A1 | 6/2014 | Bruder et al. |
| 2014/0257271 A1 | 9/2014 | Mayse et al. |
| 2014/0274614 A1 | 9/2014 | Min et al. |
| 2014/0275705 A1* | 9/2014 | Virshup ............... A61B 6/032 |
| | | 600/1 |
| 2014/0275924 A1 | 9/2014 | Min et al. |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2014/0316269 A1 | 10/2014 | Zhang et al. |
| 2014/0331771 A1 | 11/2014 | Baba et al. |
| 2015/0005613 A1 | 1/2015 | Kim et al. |
| 2015/0005637 A1* | 1/2015 | Stegman ............... A61B 8/5223 |
| | | 600/449 |
| 2015/0029819 A1 | 1/2015 | Yacoubian |
| 2015/0092814 A1 | 4/2015 | Wolfgruber |
| 2015/0175747 A1 | 6/2015 | Liu et al. |
| 2015/0231414 A1 | 8/2015 | Ein-Gal |
| 2015/0253266 A1 | 9/2015 | Lucon et al. |
| 2015/0289931 A1 | 10/2015 | Puryear et al. |
| 2016/0000345 A1 | 1/2016 | Kobayashi et al. |
| 2016/0045121 A1 | 2/2016 | Akingba et al. |
| 2016/0109393 A1 | 4/2016 | Mandelis et al. |
| 2016/0121142 A1* | 5/2016 | Zhang ............... A61B 8/4254 |
| | | 601/2 |
| 2016/0299108 A1 | 10/2016 | Bisle et al. |
| 2016/0317122 A1 | 11/2016 | Dos Santos Mendonca et al. |
| 2017/0027460 A1 | 2/2017 | Shimada et al. |
| 2017/0035310 A1 | 2/2017 | Shimada et al. |
| 2017/0097280 A1 | 4/2017 | Drescher et al. |
| 2017/0212066 A1 | 7/2017 | Thompson et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |

(56) References Cited

U.S. PATENT DOCUMENTS

| | | |
|---|---|---|
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |

FOREIGN PATENT DOCUMENTS

| | | |
|---|---|---|
| EP | 0679371 A1 | 11/1995 |
| EP | 1265223 A2 | 12/2002 |
| EP | 1579889 | 9/2005 |
| EP | 1579889 A1 | 9/2005 |
| EP | 1847294 A1 | 10/2007 |
| EP | 2359764 | 8/2011 |
| EP | 2430996 | 3/2012 |
| EP | 1503685 | 10/2012 |
| EP | 1299035 | 2/2013 |
| EP | 2842604 | 3/2015 |
| EP | 2968984 | 8/2016 |
| EP | 2995250 | 10/2019 |
| EP | 3799931 | 4/2021 |
| JP | H05220152 A | 8/1993 |
| JP | 2007000218 A | 1/2007 |
| WO | WO-9502361 A1 | 1/1995 |
| WO | WO-9731364 A1 | 8/1997 |
| WO | WO 9902096 | 1/1999 |
| WO | WO-9948621 A2 | 9/1999 |
| WO | WO-0134018 A2 | 5/2001 |
| WO | WO 01/95820 | 12/2001 |
| WO | WO 02/005897 | 1/2002 |
| WO | WO 2002/019934 | 3/2002 |
| WO | WO-02069805 A1 | 9/2002 |
| WO | WO 03/022167 | 3/2003 |
| WO | WO 03/051450 | 6/2003 |
| WO | WO-2005030295 A2 | 4/2005 |
| WO | WO-2006003606 A2 | 1/2006 |
| WO | WO 2006/041881 | 4/2006 |
| WO | WO 2006/060053 | 6/2006 |
| WO | WO-2006121447 A2 | 11/2006 |
| WO | WO-2006129099 A1 | 12/2006 |
| WO | WO 2007/014003 | 2/2007 |
| WO | WO-2008144274 A2 | 11/2008 |
| WO | WO-2009003138 A1 | 12/2008 |
| WO | WO-2009018351 A1 | 2/2009 |
| WO | WO-2009018394 A1 | 2/2009 |
| WO | WO-2009081339 A1 | 7/2009 |
| WO | WO-2011053757 A1 | 5/2011 |
| WO | WO-2011053772 A1 | 5/2011 |
| WO | WO-2014164363 A1 | 10/2014 |

OTHER PUBLICATIONS

Billard, B.E., et al., "Effects of Physical Parameters on High Temperature Ultrasound Hyperthermia," Ultrasound in Med. & Biol. vol. 16, No. 4, pp. 409-420, 1990.

Chapelon, J.Y., "Treatment of Localised Prostate Cancer with Transrectal High Intensity Focused Ultrasound," European Journal of Ultrasound 9, 31-38, 1999.

Coates, Paul et al., "Time, Temperature, Power, and Impedance Considerations for Radiofrequency Catheter Renal Denervation," Cardiovascular Revascularization Medicine 42, 171-177 (2022).

Deardorff, Dana et al., "Ultrasound Applicators with Internal Cooling for Interstitial Thermal Therapy," SPIE vol. 3594, 36-46, Jan. 1999.

Diederich, et al., "Catheter-based Ultrasound Applicators for Selective Thermal Ablation: progress towards MRI-guided applications in prostate," International Journal of Hyperthermia, 20:7, 739-756.

Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.

European Search Report dated Nov. 19, 2018 in European Patent Application No. 218186547.

Fan, Xiaobing, et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.

Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.

Papadopoulos, N., "Evaluation of a Small Flat Rectangular Therapeutic Ultrasonic Transducer Intended for Intravascular Use," Ultrasonics 74, 196-203, 2017.

Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.

Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.

Sato, Yu, et al., "Translational Value of Preclinical Models for Renal Denervation: a histological comparison of human versus porcine renal nerve anatomy," EuroIntervention, 18, e1120-e1128, 2023.

Tanaka, Kazushi et al., "A New Radiofrequency Thermal Balloon Catheter for Pulmonary Vein Isolation," Journal of the American College of Cardiology vol. 38, No. 7, 2001.

Ulmsten, Ulf et al., "The Safety and Efficacy of MenoTreat™, a new balloon device for thermal endometrial ablation," Acta Obstet Gynecol Scand 2001; 80: 52-57.

U.S. Appl. No. 60/747,137, File History.

U.S. Appl. No. 60/808,306, File History.

U.S. Appl. No. 61/405,472, File History.

Accornero, Neri et al., "Selective Activation of Peripheral Nerve Fibre Groups of Different Diameter By Triangular Shaped Stimulus Pulses", J. Physiol. (1977), 273, _ 539-560, 22 Q9S.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

American Heart Association—Pulmonary Hypertension: High Blood Pressure in the Heart-to-Lung System, (last reviewed Oct. 31, 2016).

Appeal Brief of Patent Owner from Reexamination 95-002,110.

Aytac, et al., "Correlation Between the Diameter of the Main Renal Artery and the Presence of an Accessory Renal Artery", J Ultrasound Med 22:433-439, 2003 (.

Azizi, Michel et al., Ultrasound renal denervation for hypertension resistant to a triple medication pill (RADIANCE-HTN TRIO): a randomised, multicentre, single-blind, sham-controlled trial, 397 Lancet 2476 (2021).

Bailey, M.R. et al., Physical Mechanisms of the Therapeutic Effect of Ultrasound (A Review), Acoustical Physics, vol. 49, No. 4, 2003, pp. 369-388.

Bengel, et al., Serial Assessment of Sympathetic Reinnervation After Orthotopic Heart Transplantation; A Longitudinal Study Using PET and C-11 Hydroxyephedrine, Circulation. 1999;99:1866-1871.

Bhatt, D.L., et al., A Controlled Trial of Renal Denervation for Resistant Hypertension, New England J. Med., 370:1393-1401 (2014).

Bhatt, Deepak L. et al., Long-term outcomes after catheter-based renal artery denervation for resistant hypertension: final follow-up of the randomised SYMPLICITY HTN-3 Trial, 400 Lancet 1405 (2022).

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhrol Dial Transplant, vol. 19, No. 6, 1354-1357 (2004).

(56) References Cited

OTHER PUBLICATIONS

Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, May 2001, 1041-1049 (2001).
Camasao, D.B. et al., The mechanical characterization of blood vessels and their substitutes in the continuous quest for physiological-relevant performances: A critical review, Materials Today Bio, vol. 10 (2021).
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Charlesworth, Peter et al., Renal Artery Injury From a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Corrected Patent Owner's Response to Office Action, dated May 10, 2013, from File History of Inter Partes Reexamination 95/002,110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Curriculum Vitae of Dr. John M. Moriarty.
Curriculum Vitae of Dr. Michael Bohm.
Curriculum Vitae of Farrell Mendelsohn.
Curriculum Vitae of Dr. Chris Daft.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner'sResponse, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald F. et al., "Neural Control of Renal Function", 77 Physiological Reviews No. 1, 75 (1997).
Dibona, Gerald, Sympathetic Nervous System and Kidney in Hypertension, Current Opinion in Nephrology and Hypertension, vol. 11, 197-200 (2002).
Diederich, et al., Ultrasound Catheters For Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003 ; 50(1): 41-50_doi:10.1109fTBME.2002.807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019—Preliminary Remarks for EP appeal No. T2680/16-3.3.4.01.
European Communication dated Oct. 23, 2013 in EP Application No. 12180431.4.
European Office Action re Application No. 12180431.4.
European Patent No. 12167931, Claims of the Main Request dated Sep. 30, 2016.
European Search Report (supplementary) dated Feb. 17, 2016 in European Patent Application No. 14775754.6.
European Search Report dated Mar. 1, 2021 in European Patent Application No. 20202272.9.
European Search Report for Patent Application No. EP12180431 dated Jan. 17, 2013.
Fengler, Karl et al., A Three-Arm Randomized Trial of Different Renal Denervation Devices and Techniques in Patients With Resistant Hypertension (RADIOSOUND-HTN), 139 Circulation 590 (2019).
File History to EP1802370B1 Part 1.
File History to EP1802370B1 Part 2.
File History to EP1802370B1 Part 3.
Gallitto, Enrico et al., Renal Artery Orientation Influences the Renal Outcome in Endovascular Thoraco—abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS—guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).

(56) References Cited

OTHER PUBLICATIONS

Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R.R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, S.K.S. and Wilbur, D. EDS, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA—Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, MASSDEVICE (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. 10 Oct. 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lee, Jong Deok et al., MR imaging—histopathologic correlation of radiofrequency thermal ablation lesion in a rabbit liver model: observation during acute and chronic stages, 2 Korean J. Radiol. 151 (2001).
Levin, S., et al., ARDIAN: Succeeding Where Drugs Fail—Treating Hypertension in the Cath Lab, In Vivo, 27:23 (2009).
Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).
Marine, Joseph E., Catheter ablation therapy for supraventricular arrhythmias, 298 JAMA 2768 (2007).
Martin, Louis K. et al., Long-term Results of Angioplasty in 110 Patients with Renal Artery Stenosis, Journal of Vascular and Interventional Radiology, vol. 3, No. 4, 619-626 (1992).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.
Matsumoto, Edward D. et al., Short-term efficacy of temperature-based radiofrequency ablation of small renal tumors, 65 Urology 877 (2005).
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic Inc., Renal Denervation (RDN): Novel Catheter-Based Treatment for Hypertension, Scientific Background, 2011.
Medtronic Scientific Background, Hypertension and the Symplicity Renal Denervation System.
Medtronic, Symplicity RDN Common System Q&A.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization For Ablation of Function In Renal Failure And Hypertension, Postgraduate Med. J. 65, 729-734 (1989) .
Mitchell, et al., "The Renal Nerves" British Journal of Urology, Read by invitation at the Sixth Annual Meeting of the British Association of Urological Surgeons on Jun. 30, 1950.
Morrissey, D. M. "Sympathectomy in the treatment of hypertension." Lancet, CCLXIV:403-408 (1953).
Nair et al., "The Need for and the Challenges of Measuring Renal Sympathetic Nerve Activity," Heart Rhythm 2016; 13:1166-1171.
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Notice of Deposition of Tucker, filed Dec. 30, 2022 in the Patent Trial and Appeal Board, United States Patent and Trademark Office, Petition No. PTAB-IPR2022-00431.
Notice of Deposition of van der Weide, filed Dec. 30, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.

(56) References Cited

OTHER PUBLICATIONS

Nozawa, T., et al. "Effects of long-term renal sympathetic denervation on heart failure after myocardial infarction in rats." Heart Vessels, 16:51-56 (2002).
Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").
Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Olsson, R. et al., "A Three-Dimensional Neural Recording Microsystem With Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.
Order Setting Oral Hearing 37 C.F.R. § 42.70, dated Mar. 24, 2023 in the Patent Trial and Appeal Board, United States Patent and Trademark Office, Petition No. PTAB-IPR2022-00431.
Osborn, J., "Catheter-Based Renal Nerve Ablation as a Novel Hypertension Therapy, Lost, and Then Found," in Translation.
Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).
Page, Irvine H. & George J. Heuer, The Effect of Renal Denervation on Patients Suffering from Nephritis, 14 J. Clinical Investigation 443 (1935) (received for publication in 1935).
Papademetriou, Vasilios et al., Renal Sympathetic Denervation for the Treatment of Difficult-to-Control or Resistant Hypertension, 2011 Int. J. Hypertension, Article 196518 (2011).
Papademetriou, et al., "Renal Sympathetic Denervation: Hibernation or Resurrection?", Cardiology 2016 ; 135, 11 pgs.
Pappone C, et al., "Circumferential radiofrequency ablation of pulmonary vein ostia: a new anatomic approach for curing atrial fibrillation", Circulation. 2000; 102(21): 2619-2628. (2000).
Patent Owner's Amended Objections to Evidence Under 37 C.F.R. §42.64.
Patent Owner's Mandatory Notice, filed Feb. 3, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Power of Attorney, filed Feb. 3, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martinek, Martin, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications, "Biological Procedures Online, Jan. 2006, 25 pages.
Romanes, G.J., Cunningham's Textbook of Anatomy (11th ed. 1972).
Ryan, Thomas et al., Proceedings of Thermal Treatment of Tissue with Image Guidance, Progress in Biomedical Optics, vol. 3594 (1999).
Ryan, Thomas P._ Thermal Treatment of Tissue with Image Guidance; Ultrasound Catheters For Circumferential Cardiac Ablation 1999.
Ryan, Steve, What are the Risks Associated with a Pulmonary Vein Ablation Procedure?, Atrial Fibrillation: Resources for Patients (last accessed Oct. 18, 2022).

(56) References Cited

OTHER PUBLICATIONS

Sakakura, Kenichi et al., Anatomic Assessment of Sympathetic Peri-Arterial Renal Nerves in Man, Journal of the American College of Cardiology, vol. 64, No. 7, 635-643 (2014).

Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.

Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").

Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.

Schmieder, Ronald E., Renal denervation in patients with chronic kidney disease: current evidence and future perspectives, Nephrol. Dial. Transplant. gfac189 (2022).

Schneider, Peter, Endovascular Skills: Guidewire and Catheter Skills for Endovascular Surgery, 2nd ed., Marcel Dekker, Inc., New York, NY (2003).

Schneider, Peter A., Endovascular Skills, Quality Medical Publishing, Inc., 1998 ("Schneider").

Schmidt, Boris, et al., "Pulmonary Vein Isolation by High Intensity Focused Ultrasound," Indian Pacing and Electrophysiology Journal, pp. 126-133 (2006).

Shimizu, Kazumasa et al., Sympathetic Dysfunction in Heart Failure, Bailliere's Clinical Endocrinology and Metabolism, vol. 7, No. 2 (1993).

Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").

Slide deck from Medtronic Circulatory System Devices Panel Meeting, General Issues Panel: Clinical Evaluation of Anti-Hyperintensive Devices (Dec. 5, 2018).

Selected documents from the File History of Inter Partes Reexamination 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Smithwick, R. H., et al., "Splanchnicectomy for essential hypertension." J. Am. Med. Assoc., 152:1501-1504 (1953).

Stella, A., et al. "Effects of reversible renal denervation on haemodynamic and excretory functions of the ipsilateral and contralateral kidney in the cat." J Hypertension, 4: 181-188 (1986)("Stella").

Stipulation Modifying Schedule, dated Dec. 30, 2022 in the Patent Trial and Appeal Board, United States Patent and Trademark Office, Petition No. PTAB-IPR2022-00431.

Stipulation Modifying Schedule, dated Feb. 16, 2023 in the Patent Trial and Appeal Board, United States Patent and Trademark Office, Petition No. PTAB-IPR2022-00431.

Stoeckel, D. et al., A Survey of Stent Designs, Min Invas Ther & Allied Technol 2002: 11(4) 137-147 (2002).

Swartz, John F. et al., Radiofrequency Endocardial Catheter Ablation of Accessory Atrioventricular Pathway Atrial Insertion Sites, 87 Circulation 487 (1993).

Tank, J. et al., "Spike Rate of Multi-Unit Muscle Sympathetic Nerve Fibers Following Catheter-Based Renal Nerve Ablation," J Am. Soc Hypertens, Oct. 2015 ; 9(10): 794-801 . doi:10.1016/j.jash.2015. 07.012.

Teigen et al., Segmental Renal Artery Embolization for Treatment of Pediatric Renovascular Hypertension, J. Vasco Interv. Radiol. 3, 111-7 (1992).

Thatipelli, Mallik R., et al., CT angiography of renal artery anatomy for evaluating embolic protection devices, 18 J. Vasc. Interv. Radiol. 842 (2007).

The Doctors and Experts at WebMD, Webster's New World Medical Dictionary (3rd ed. 2008) ("WebsterMD").

Transcript of the Mar. 2, 2023 deposition of Dr. John Moriarty.

Transcript of the Mar. 3, 2023 deposition of Dr. Chris Daft.

Transcript of deposition of the Jan. 1, 2023 deposition of Dr. Robert Tucker.

Transcript of the Jan. 14, 2023 deposition of Dr. Daniel van der Weide.

Transcript of the Sep. 30, 2022 deposition of Dr. Chris Daft.

Transcript of the Oct. 1, 2022 deposition of Dr. Farrell Mendelsohn.

Tsao, Hsuan-Ming et al., Evaluation of Pulmonary Vein Stenosis after Catheter Ablation of Atrial Fibrillation, 6 Card. Electrophysiol. Rev. 397 (2002).

Turner, et al., "Initial Experience Using the Palmaz Corinthian Stent for Right Ventricular Outflow Obstruction in Infants and Small Children", Catheterization and Cardiovascular Interventions 51:444-449 (2000).

Uchida, et al., "Effect of radiofrequency catheter ablation on parasympathetic denervation: A comparison of three different ablation sites." PACE, 21 :2517-2521 (1998).

Vaezy, Shahram et al., Image-Guided Acoustic Therapy, Annual Review Biomedical Engineering, vol. 3, 375-390 (2001).

Valente, John F. et al., Laparoscopic renal denervation for intractable ADPKD-related pain, 16 Nephrol. Dial. Transplant. 160 (2001).

Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").

Wanchoo, Nishey, Medtronic Gets European and Australian Approval for Symplicity Spyral Multi-Electrode Renal Denervation Catheter, Medgadget (2013).

Weinstock, Marta et al., "Renal Denervation Prevents Sodium Retention and Hypertension in Salt-Sensitive Rabbits with Genetic Baroreflex Impairment", 90 Clinical Science 287 (1996).

Xu, J. et al., "A Bidirectional Neuromodulation Technology for Nerve Recording and Stimulation, Micromachines," vol. 9, 1 1 538. Oct. 23, 2018. doi:10.3390/mi9110538.

Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

Zazgornik, "Bilateral Nephrectomy: The best, but often overlooked, treatment for refractory hypertension in hemodialysis patients," Am. J. Hypertension, 11:1364-1370 (1998).

Ziegler et al., Sources of Urinary Catecholamines in Renal Denervated Transplant Recipients, 8 J. Hypertension No. 10, 927 (1990).

U.S. Appl. No. 17/453,636, filed Nov. 4, 2021.

U.S. Appl. No. 10/408,665.

U.S. Appl. No. 60/624,793.

U.S. Appl. No. 60/370,190.

U.S. Appl. No. 60/415,575.

U.S. Appl. No. 60/442,970.

U.S. Appl. No. 60/616,254.

U.S. Appl. No. 60/816,999.

U.S. Appl. No. 14/683,966, Non Final Office Action mailed Jun. 12, 2017, 14 pgs.

U.S. Appl. No. 14/683,966, Response filed Nov. 10, 2017 to Non Final Office Action mailed Jun. 12, 2017, 13 pqs.

U.S. Appl. No. 14/683,966, Notice of Allowance mailed Jan. 31, 2018, 8 pgs.

U.S. Appl. No. 14/683,966, PTO Response to Rule 312 Communication mailed Mar. 29, 2018, 2 pgs.

U.S. Appl. No. 14/683,966, 312 Amendment filed Mar. 13, 2018, 10 pgs.

U.S. Appl. No. 14/683,966, Corrected Notice of Allowance mailed May 22, 2018, 4 pgs.

U.S. Appl. No. 15/204,349, Preliminary Amendment filed Nov. 30, 2016, 3 pgs.

U.S. Appl. No. 15/204,349, Restriction Requirement mailed May 17, 2018, 7 pgs.

U.S. Appl. No. 15/204,349, Response filed Jun. 5, 2018 to Restriction Requirement mailed May 17, 2018, 7 pgs.

(56) References Cited

OTHER PUBLICATIONS

U.S. Appl. No. 15/204,349, Non Final Office Action mailed Nov. 27, 2018, 14 pgs.
U.S. Appl. No. 15/204,349, Response filed Feb. 27, 2019 to Non Final Office Action mailed Nov. 27, 2018, 10 pgs.
U.S. Appl. No. 15/204,349, Final Office Action mailed Apr. 22, 2019, 16 pgs.
U.S. Appl. No. 15/204,349, Response filed Jun. 24, 2019 to Final Office Action mailed Apr. 22, 2019, 12 pgs.
U.S. Appl. No. 15/204,349, Advisory Action mailed Jul. 9, 2019, 5 pgs.
U.S. Appl. No. 15/299,694, Restriction Requirement mailed Aug. 6, 2018, 6 pgs.
U.S. Appl. No. 15/299,694, Response filed Oct. 8, 2018 to Restriction Requirement mailed Aug. 6, 2018, 7 pgs.
U.S. Appl. No. 15/299,694, Non Final Office Action mailed Nov 27, 2018, 15 pgs.
U.S. Appl. No. 15/299,694, Response filed Feb. 27, 2019 to Non-Final Office Action mailed Nov. 27, 2018, 10 pgs.
U.S. Appl. No. 15/299,694, Final Office Action mailed Apr. 22, 2019, 16 pgs.
U.S. Appl. No. 15/299,694, Response filed Jun. 24, 2019 to Final Office Action mailed Apr. 22, 2019, 11 pgs.
U.S. Appl. No. 15/299,694, Advisory Action mailed Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement mailed Nov. 20, 2019, 8 pages.
U.S. Appl. No. 15/943,354, Response filed Dec. 19, 2019 to Restriction Requirement mailed Nov. 20, 2019, 8 pages.
U.S. Appl. No. 15/943,354, Non Final Office Action mailed Jan. 13, 2020, 6 pages.
U.S. Appl. No. 15/943,354, Non Final Office Action mailed Apr. 20, 2020, 7 pages.
U.S. Appl. No. 15/996,978, Preliminary Amendment filed Jun. 5, 2018, 11 pgs.
U.S. Appl. No. 15/996,978, Restriction Requirement mailed Feb. 7, 2020, 7 pages.
U.S. Appl. No. 15/996,978, Response filed Apr. 6, 2020 to Restriction Requirement mailed Feb. 7, 2020, 8 pages.
U.S. Appl. No. 15/996,978, Restriction Requirement mailed Apr. 16, 2020, 8 pages.
U.S. Appl. No. 15/996,978, Response filed May 1, 2020 to Restriction Requirement mailed Apr. 16, 2020, 8 pgs.
U.S. Appl. No. 15/996,978, Non Final Office Action mailed Jun. 11, 2020, 8 pages.
U.S. Appl. No. 16/517,180, Preliminary Amendment filed Jul. 19, 2019, 12 pgs.
File History of U.S. Appl. No. 12/754,337.
File History to U.S. Pat. No. 9,943,666.
File History to U.S. Pat. No. 9,981,108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.
Calkins, Hugh et al., "Temperature Monitoring During Radiofrequency Catheter Ablation Procedures Using Closed Loop Control," Circulation vol. 90, No. 3, p. 1279-1286, Sep. 1994.
Deardorff, Dana L. et al., "Control of interstitial thermal coagulation: Comparative evaluation of microwave and ultrasound applicators," Medical Physics vol. 28, No. 1, p. 104-117, Jan. 2001.
Dinerman, Jay L. et al., "Temperature Monitoring During Radiofrequency Ablation," Journal of Cardiovascular Electrophysiology, vol. 7 No. 2, p. 163-173, Feb. 1996.
Esler, Murray et al., "The future of renal denervation," Autonomic Neuroscience: Basic and Clinical, vol. 204, p. 131-138, May 2017.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Fry, William J., "Action of Ultrasound on Nerve Tissue—A review," The Journal of the Acoustical Society of America, vol. 25 No. 1, p. 1-5, Jan. 1953.
Fry, Frank J., "Precision High Intensity Focusing Ultrasonic Machines for Surgery," High Intensity Focused U.S., 152-156, Sep. 6-7, 1957.
Haines, David, "Biophysics of Ablation: Application to Technology," Journal of Cardiovascular Electrophysiology, vol. 15, No. 10, p. S2-S11, Oct. 2004.
Hynynen, K. et al., "Design of Ultrasonic Transducers for Local Hyperthermia," Ultrasound in Med. & Biol., vol. 7, No. 4, p. 397-402, Feb. 1981.
Hynynen, K. et al., "Temperature measurements during ultrasound hyperthermia," Medical Physics vol. 16, No. 4, p. 618-626, Jul./Aug. 1989.
Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.
Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.
Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59- 62, Oct. 2013.
Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (SPYRAL HTN OFF-MED) and presence (SPYRAL HTN ON-MED) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.

(56) References Cited

OTHER PUBLICATIONS

Stauffer, P.R. et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

\* cited by examiner

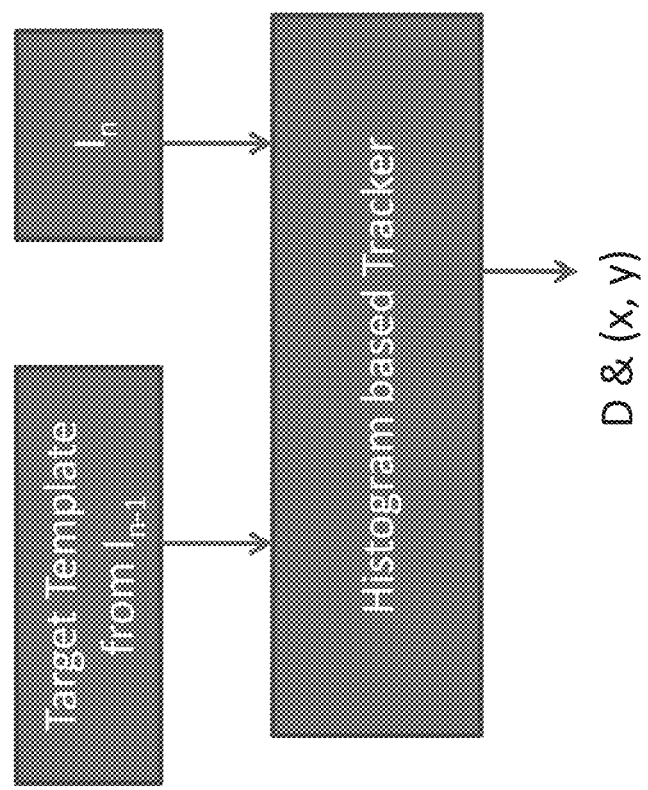

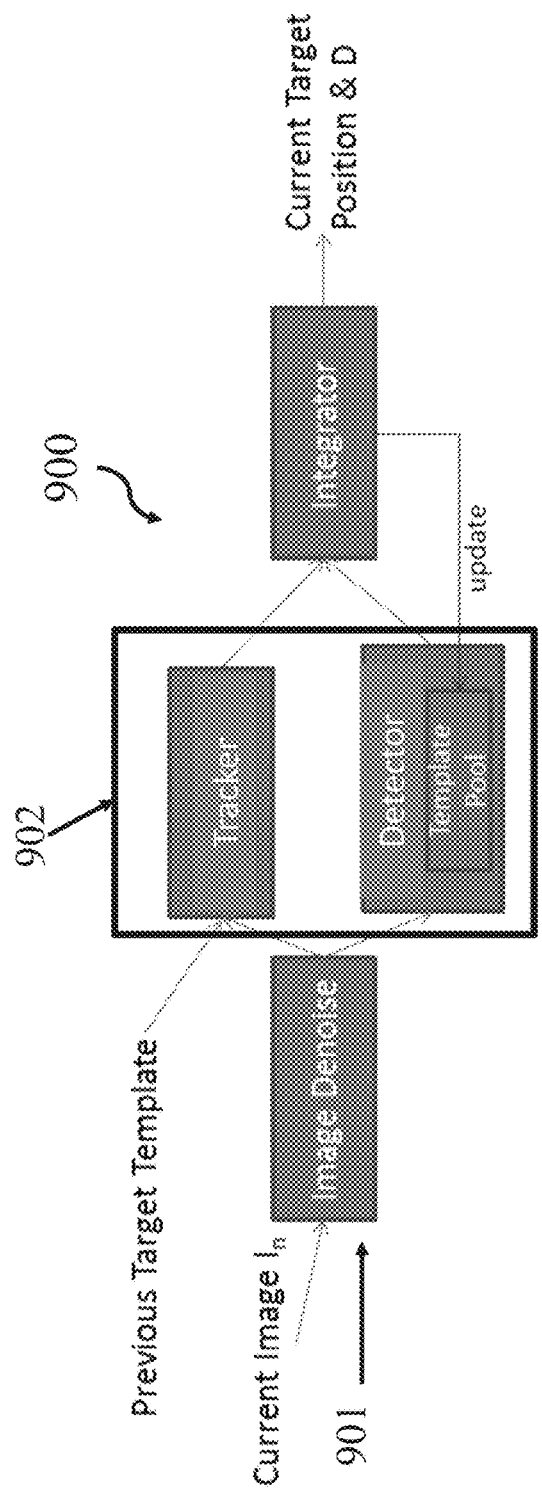
Figure 9A
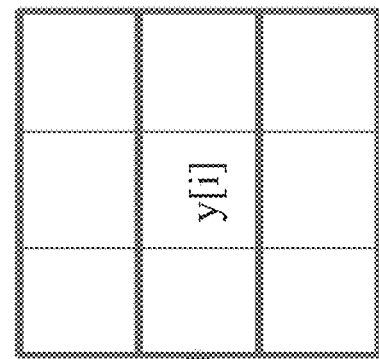
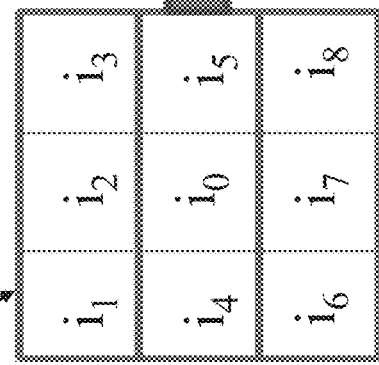
Figure 9B

SYSTEMS AND METHODS FOR REAL-TIME TRACKING OF A TARGET TISSUE USING IMAGING BEFORE AND DURING THERAPY DELIVERY

CROSS-REFERENCE TO RELATED APPLICATIONS

This application is a divisional application of U.S. application Ser. No. 14/929,056, filed Oct. 30, 2015, now U.S. Pat. No. 10,925,579, which claims priority to and the benefit of U.S. Provisional Patent Application No. 62/075,487, filed on Nov. 5, 2014, the entire disclosure of each of the above applications is expressly incorporated by reference herein.

This application is related to international PCT patent application serial No. PCT/US2014/022141, titled "TRANSDUCERS, SYSTEMS, AND MANUFACTURING TECHNIQUES FOR FOCUSED ULTRASOUND THERAPIES", filed on Mar. 7, 2014, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to the imaging field, and more specifically to a new and useful system and method for real-time tracking of a target tissue using imaging before and during therapy delivery.

BACKGROUND

Therapeutic energy delivery from a distance involves transmission of energy waves to affect a target tissue inside a patient's body. Therapeutic delivery of ultrasound waves has been used in a wide variety of therapeutic interventions, including lithotripsy, drug delivery, cancer therapy, thrombolysis, and tissue ablation. Non-invasive delivery of focused energy may allow for more efficient delivery of energy to the target tissue, improved cost effectiveness of treatment, minimized trauma to the patient's body, and improved recovery time.

Delivering energy over a distance requires targeting accuracy and technological flexibility while minimizing invasiveness into the patient. However, current methods fail to adequately track the target tissue motion while concurrently delivering the energy or therapy. A tissue in the body moves relative to the energy-delivering source from either the unintended patient body motion or the internal organs' motion due to heartbeat, breathing, blood flow, or other physiological functions. Current methods stop delivering the energy or therapy when the tissue moves out of focus or visibility due, at least, to breathing or shadows and reinitiates energy or therapy delivery when the tissue reemerges. The stopping and starting of therapy or energy delivery can have unintended consequences for the patient, such as variable dosing, uneven or insufficient therapy delivery to the target tissue, and prolonged procedure times.

Conventional ultrasound systems for tracking a targeted soft tissue motion have a much lower signal-to-noise ratio. Further, the shape of a target image can change more as it moves within the image because of ultrasound beam scan orientation, tissue deformation, ultrasound signal distortion and other factors. Controlling these factors is desirable for effective and accurate therapeutic energy delivering to the target tissue. Since soft tissue deforms at a macroscopic level, conventional tracking systems cannot adequately track such tissue deformation and motion. Further, tracking and energy delivery will halt when a conventional system loses the target tissue, due to, for example, rib shadows or deep breaths that move the target out of sight. This happens regularly in conventional systems. Conventional systems are not configured to deal with these motions, and even more importantly they are not configured to properly recover tracking once the image reappears, requiring user input to relocate the lost target tissue in the image.

Thus, there is a need for a new and useful system and method for tracking a target tissue using imaging before and during therapy delivery. In particular, there is a need for new and useful systems and methods configured to accommodate when tissue moves out of focus or visibility, and even more importantly configured to automatically recover tracking when the image reappears. This invention provides such a new and useful system and method.

SUMMARY

A system for identifying at least one anatomical structure and tracking a motion of the at least one anatomical structure using imaging before and during delivery of a therapy to a patient, includes: an imaging module configured to identify a location and a feature of a region of the anatomical structure in an image, wherein the imaging module comprises a tracker, a detector, and an integrator; and a therapy module comprising an ultrasound treatment transducer configured to deliver the therapy to a target tissue in the patient.

Optionally, the imaging module is configured to, in real-time, track the anatomical structure using a feature identification technique.

Optionally, the imaging module is configured to use a histogram of the anatomical structure in the image, or a feature matching technique.

Optionally, the imaging module is configured to identify a location of the target tissue to be treated by the therapy module.

Optionally, the tracker is configured to identify a new location or a new feature of the region of the anatomical structure in response to a change in the location and the feature of the region of the anatomical structure.

Optionally, the detector is configured to identify a shape, a location, and a feature of the region of the anatomical structure.

Optionally, the tracker, detector, and integrator are implemented in graphics processor unit (GPU), field-programmable gate array (FPGA) or digital signal processor (DSP) or any other units containing computation capabilities.

Optionally, the therapy module is configured to function concurrently with the imaging module.

Optionally, the therapy module is configured to deliver therapy to the target tissue despite a change in the location or the feature of the region of the anatomical structure.

Optionally, the anatomical structure comprises the target tissue.

Optionally, at least one of breathing, blood flow, conscious movement, or unconscious movement of the patient changes the location and/or the feature of the region of the anatomical structure.

Optionally, the imaging module is configured to identify the location and the feature of the region of the anatomical structure in less than 1 second.

Optionally, the imaging module is configured to identify the location and the feature of the region of the anatomical structure in less than 5 milliseconds.

Optionally, the target tissue comprises a renal artery.

Optionally, the ultrasound treatment transducer is configured to provide renal denervation.

Optionally, the imaging module is configured to track the region of the anatomical structure is using a B-mode image, Harmonic Imaging, or 3D ultrasound imaging.

Optionally, the imaging module is configured to track the region of the anatomical structure using a color Doppler image, a color power Doppler image, or a directional color power Doppler mode image.

Optionally, the system further includes a filter, wherein the filter is configured to reduce noise in the image, such that the imaging module can determine the location and the feature of the region of the anatomical structure in the image.

Optionally, the filter is configured to provide a filtered image that is visible to the tracker, the detector, or both the tracker and detector.

Optionally, the system further includes a user interface for allowing a user to choose between viewing the filtered image or an unfiltered image.

Optionally, the location is an x and y coordinate.

Optionally, the location is an x, y, and z coordinate.

Optionally, the image is an ultrasound image.

Optionally, the integrator is configured to integrate results from the tracker and detector and direct the therapy module to deliver the therapy to the target tissue.

Optionally, the location is in a plane.

Optionally, the location is in a three-dimensional space.

Optionally, a plane of movement of the anatomical structure is substantially parallel to an imaging plane of the imaging module.

Optionally, the feature includes one or more of a characteristic, intensity, density, contrast, and shape of the region of the anatomical structure.

Optionally, the imaging module and the therapy module are configured to function consecutively using an interleaving mechanism.

Optionally, the imaging module and the therapy module are configured to function concurrently using a continuous mechanism.

Optionally, the therapy module is configured to predict a future location or a future feature of the target tissue and to deliver the therapy to the target tissue when the target tissue reaches the future location or the future feature.

Optionally, the therapy module is configured to provide lithotripsy.

Optionally, the lithotripsy comprises treatment of a kidney stone, gallstone, bile duct stone, or ureter stone.

Optionally, the tracker comprises a short-term detector.

Optionally, the detector comprises a long-term detector.

A system for tracking a renal artery during delivery of an ultrasound therapy to a patient, includes: an imaging module configured to identify a location and a feature of a region of an anatomical structure in an ultrasound image, wherein the imaging module comprises a tracker, a detector, and an integrator; and a therapy module comprising an ultrasound treatment transducer configured to deliver the ultrasound therapy to the renal artery, wherein the ultrasound treatment transducer is configured to be mechanically moved and/or electronically controlled.

Optionally, the ultrasound treatment transducer is configured to be moved by a motion control mechanism to move the ultrasound treatment transducer.

Optionally, the ultrasound treatment transducer comprises a full circular annular phased array.

Optionally, the ultrasound treatment transducer comprises a partial circular annular phased array.

Optionally, the ultrasound treatment transducer is configured to be directed and moved to guide therapeutic energy to the renal artery.

Optionally, the ultrasound treatment transducer comprises a two-dimensional array and is configured to move therapy focus by a three-dimensional electronic control mechanism to guide therapeutic energy to the renal artery.

Optionally, the ultrasound treatment transducer is configured to be moved by a mechanical control mechanism to guide therapeutic energy to the renal artery.

A method for imaging during delivery of a therapy, includes: acquiring an image of a body portion of a patient; identifying a region of an anatomical structure that has a relationship to a target tissue in the image; tracking a location and/or a feature of the region of the anatomical structure in the image; integrating results from the act of tracking; generating a template library to cover possible changes of the location and/or changes of the feature of the region of the anatomical structure; and delivering the therapy to the target tissue while tracking the region of the anatomical structure in the image.

Optionally, the method further includes continuously delivering therapy to the target tissue despite a change in one or more locations and features of the region of the anatomical structure.

Optionally, the act of tracking occurs in response to a change in the location or the feature of the region of the anatomical structure.

Optionally, the region of the anatomical structure comprises the target tissue.

Optionally, at least one of breathing, blood flow, conscious movement, or unconscious movement of the patient changes the location and/or the feature of the region of the anatomical structure.

Optionally, the region of the anatomical structure is undetectable by the imaging module as a result of at least one of breathing, blood flow, conscious movement, and unconscious movement.

Optionally, the method further includes stopping imaging of the body portion of the patient when the region of the anatomical structure is undetectable.

Optionally, the method further includes automatically re-detecting the region of the anatomical structure location or feature.

Optionally, the automatically recovering step further comprises automatically recovering the region of the anatomical structure location or feature by first determining a last known location or feature of the region of the anatomical structure in the image.

Optionally, the act of tracking occurs in less than 5 milliseconds.

Optionally, the act of delivering the therapy comprises denervating renal nerves surrounding the renal artery.

Optionally, the act of delivering comprises delivering ultrasound to the target tissue.

Optionally, the act of tracking comprises using a B-mode image, Harmonic Imaging, or 3D ultrasound imaging.

Optionally, the act of tracking comprises using a color Doppler image, a color power Doppler image, or a directional color power Doppler mode image.

Optionally, the act of tracking comprises using an image in B-mode, Harmonic mode, color Doppler mode, color power Doppler mode, a combination of the B-mode, the Harmonic mode and the color Doppler mode.

Optionally, the method further includes filtering the image to obtain a filtered image, such that the anatomical structure can be tracked in the filtered image.

Optionally, the method further includes determining if a pre-existing template matches a result from the act of tracking.

Optionally, the method further includes determining if a result from the act of tracking should be updated as a new template.

Optionally, a position of the target tissue is based on the pre-existing template and a new template. For example, averaging (e.g., weighted averaging, non-weighted averaging) may be performed using information in the pre-existing template and the new template to determine the position of the target tissue.

Optionally, the method further includes generating a new template when a pre-existing template does not match a result from the act of tracking, wherein the new template defines or indicates a location and a shape of the target tissue.

A method for treatment includes: acquiring with an imaging module an image of a body portion of a patient; identifying a region of an anatomical structure that has a relationship to a target tissue in the image; tracking a location and/or a feature of the region of the anatomical structure in the image; transforming a target position of the target tissue from an imaging space associated with the imaging module to a treatment space associated with a therapy module through one or more position sensors and a transmitter; and delivering a therapy with the therapy module to the target tissue while tracking the region of the anatomical structure.

Optionally, the one or more position sensors and the transmitter are configured to link a position of an imaging transducer of the imaging module to a position of an ultrasound treatment transducer of the therapy module.

Optionally, the one or more position sensors comprises a magnetic sensor, an optical sensor, an ultrasound sensor, or a mechanical position sensor.

Optionally, the one or more position sensors are mounted on an imaging transducer of the imaging module.

Optionally, the transmitter is mounted on an imaging transducer of the imaging module.

Optionally, the one or more position sensors are mounted on an ultrasound treatment transducer of the therapy module.

Optionally, the transmitter is mounted on an ultrasound treatment transducer of the therapy module.

BRIEF DESCRIPTION OF THE DRAWINGS

FIG. 4 illustrates a flow chart for the functioning of a tracker, in accordance with a preferred embodiment;

FIGS. 9A and 9B illustrate a system including a filter for tracking a target tissue and delivering therapy to a target tissue, in accordance with a preferred embodiment;

DETAILED DESCRIPTION

Figure 1:
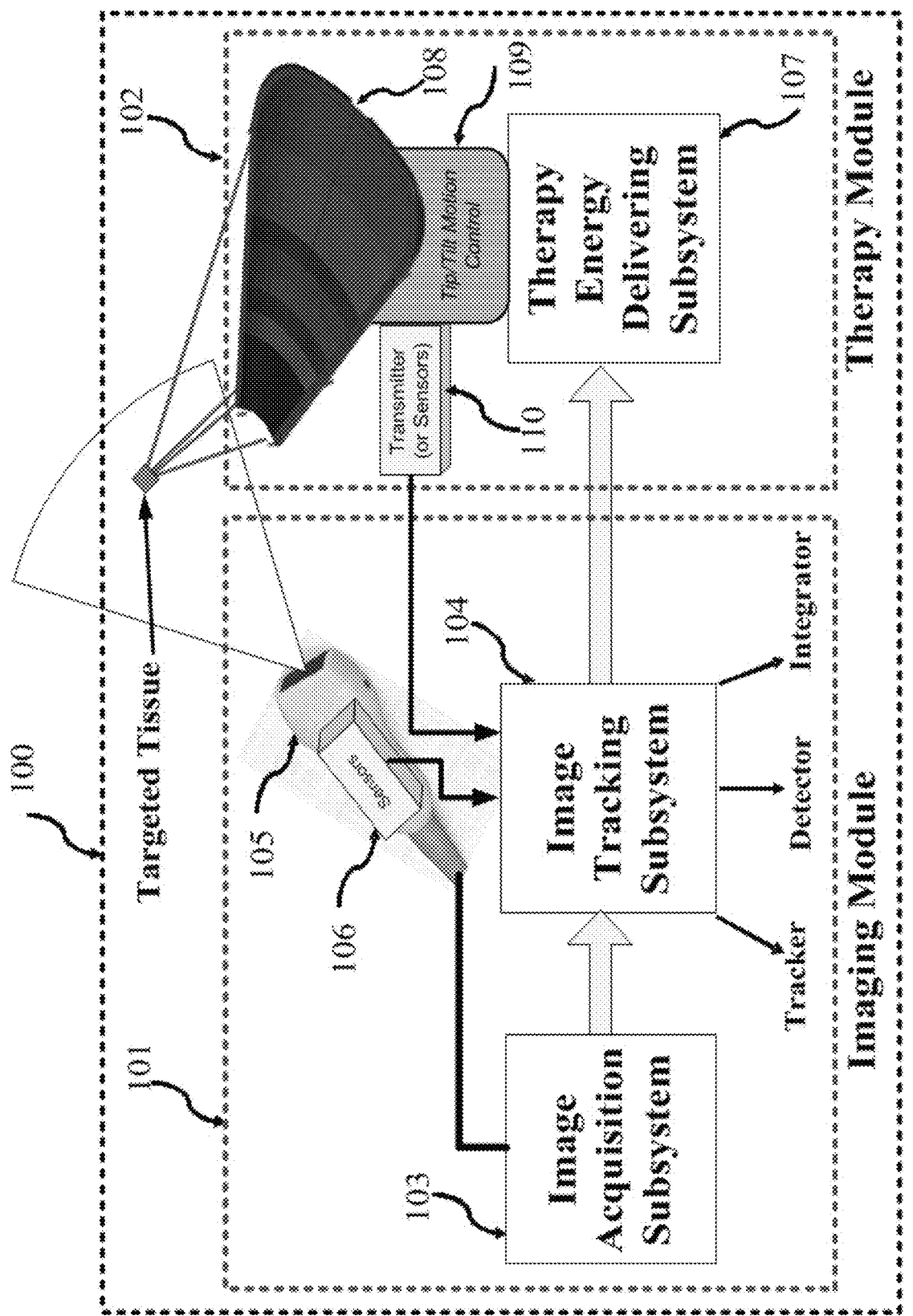
FIG. 1 illustrates a system for tracking a target tissue and delivering therapy to a target tissue, in accordance with a preferred embodiment.

The following description of the preferred embodiments of the invention is not intended to limit the invention to these preferred embodiments, but rather to enable any person skilled in the art to make and use this invention. Disclosed herein are systems and methods for identifying at least one anatomical structure and tracking the motion of the at least one anatomical structure using imaging before and during delivery of a therapy to a patient.

Described herein are systems and methods for tracking an anatomical structure in a patient and delivering therapy to an anatomical structure. The structure receiving the delivered therapy from the system is the target tissue. In some embodiments, the system may function completely non-invasively. Alternatively, the system may additionally include catheterization or otherwise surgically manipulating the patient. The system may be used to track an anatomical structure, such as an organ, blood vessel, artery, bone, blood, or any other type of anatomical structure. For example, in some embodiments, the system may function to track a kidney or renal artery of a patient. Alternatively, the system may be used to track a region of an anatomical structure, such as a curved edge or surface, a more distal or proximal portion of an organ, blood flow through a vessel, a distinguishing feature of an organ, for example glomeruli of the kidney, or any other region of interest of an anatomical structure. In some embodiments, a feature of an anatomical structure may be tracked, such as a location, shape, intensity, contrast, density, or otherwise characteristic of the anatomical structure. The location of an anatomical structure may include an x, y coordinate or an x, y, z coordinate. Alternatively, the location of the anatomical structure may be tracked in a two-dimensional plane or in three-dimensional space. The tracked anatomical structure may be a different structure than the anatomical structure receiving therapy from the system, such that a change in location or feature of the anatomical structure indicates a change in position of the target tissue. Alternatively, the anatomical structure may be the same as the target tissue, such that the target tissue is the anatomical structure that is being tracked. In some embodiments, the tracked anatomical structure may be a kidney and the target tissue receiving therapy may be a renal artery.

In some embodiments, the system may deliver therapy via ultrasound, mechanical vibrations, electromagnetic waves, lasers, X-ray or any other type of non-invasive radiation therapy. The therapy may include renal denervation, kidney stone disruption, gallstone disruption, bile duct stone disruption, ureter stone disruption, or any other type of non-invasive therapy.

In general, an anatomical structure may be lost and/or move during tracking and/or while receiving therapy. For example, an anatomical structure may be lost due to a shadow from another organ or bone structure, for example the rib cage. Alternatively or additionally, an anatomical structure may move due to breathing, blood flow, conscious movement, or unconscious movement of the patient during the procedure. In some instances, the region of the anatomical structure may become undetectable by the system as a result of breathing, blood flow, conscious movement, or unconscious movement of the patient. For example, an anatomical structure may move approximately 2 cm/second. In some instances, the anatomical structure may move substantially in a plane parallel to the plane of the system, or principal plane. Alternatively, the anatomical structure may move perpendicularly or variably relative to the system. As described herein, the system is configured to track a region of an anatomical structure despite shadows or deep breathing by a patient that moves an anatomical structure out of sight.

In some embodiments, the system may utilize an imaging module to locate the target tissue and track the position and/or movements of the target tissue, such that the therapy module can maintain its focus on the target tissue during the treatment process. In some embodiments, the imaging information may be used to confirm that the focus of the therapy module is properly positioned over the treatment region. The system then calculates the treatment parameter, such as dosing of ultrasound energy to be applied to the treatment region. For example the physician may enter the desired dosing level for a particular treatment. The system may also take into account other parameters, such as the distance of the target region from the therapy module, and calculate the appropriate ultrasound energy to apply to achieve the desired dosing at the target region. A particular treatment plan, such as a specific treatment pattern (e.g., energizing multiple spots within a treatment area), and a specific dosing routine (e.g., spreading a dose into multiple quantized delivery over a finite period of time to achieve the desired dose) may be selected. The system may then implement the treatment plan, and ultrasound energy may be delivered to the treatment region based on the treatment plan. In some embodiments, the treatment plan includes sequential lesions offset from the blood flow of a vessel and within 5 mm of one another. In another embodiment, the treatment plan includes sequential lesions offset from the blood flow and within 1 mm of each other. In another embodiment, the sequential lesions do not have an offset from one another and sequential lesions are applied atop one another in substantially the same position.

FIG. 1 illustrates a system 100 for tracking a region of an anatomical structure and delivering therapy to a target tissue, in accordance with a preferred embodiment. The system according to FIG. 1 preferably functions to image one or more anatomical structures, track a location or a feature of the anatomical structure, and delivery therapy to a target tissue. As shown in FIG. 1, a system 100 for identifying at least one anatomical structure and tracking the motion of the at least one anatomical structure using imaging before, during, or after delivery of a therapy to a patient includes an imaging module 101 and a therapy module 102. The imaging module 101 may be configured to acquire an image, identify one or more locations and/or features of an anatomical structure in the image, and/or track a location and/or feature of the anatomical structure within the image. The therapy module 102 of the system 100 may be configured to deliver therapy to a target tissue In some embodiments, the therapy module 102 may include a therapy energy delivering subsystem 107, which functions to generate controlled electrical energy to the ultrasound treatment transducer 108. In some embodiments, the ultrasound treatment transducer 108 transmits the ultrasound energy into the targeted tissue structure in a human body. In some embodiments, the ultrasound treatment transducer 108 may be a full circular annular phased array transmitting the focused ultrasound energy along the acoustic axis in depth direction into the targeted tissue structure in a human body. In other embodiments, the ultrasound treatment transducer 108 may be a section of full (e.g., partial) circular annular phased array transmitting the focused ultrasound energy along the acoustic axis in depth direction into the targeted tissue structure in a human body. For example, the transducer may have a pie shape so that the shape is less than a full circular shape. In some embodiments, the therapy module 102 may include a tip/tilt motion control unit 109 that adjusts the ultrasound treatment transducer rotation in tip and tilt directions to follow the targeted tissue motion. In other embodiments, the following of the targeted tissue motion may be accomplished by electronic control of the phasing of the ultrasound elements in the ultrasound treatment transducer, thereby obviating the need to mechanically move the ultrasound treatment transducer. In further embodiments, the control of the ultrasound energy focus may be accomplished using both electronic phasing control of ultrasound elements in the ultrasound transducer 108 and mechanical control of the movement of the ultrasound transducer 108 by the therapy module 102. In some cases, such technique may allow control of ultrasound energy focus at any position within a huge treatment volume in 3D space. In some embodiments, the therapy module 102 may further include a transmitter and/or one or more position sensors of a 3D position system 110.

In some embodiments, the imaging module 101 may include an image acquisition subsystem 103 that functions to acquire an image. In some embodiments, the image acquisition subsystem 103 may use ultrasound to acquire images of a region of an anatomical structure. In some embodiments, the imaging module 101 may further include an image tracking system 104 that functions to track a location and/or feature of an anatomical structure within the image acquired by the image acquisition subsystem 103. In some embodiments, the imaging module 101 may include an ultrasound imaging transducer 105 that transmits the ultrasound signals into the human body and receives the reflected signal from the tissue structures. In some embodiments, the imaging module 101 may further include position sensors 106 that are attached to the imaging transducer 105 to acquire the position of the imaging transducer 105 in 3D space and feed the position information to the imaging tracking subsystem 104. In some embodiments, the imaging transducer 105 may be linear, curved linear, phased, annular, or other types of imaging arrays that acquire an imaging plane inside a human body. In some embodiments, the imaging transducer 105 may be a two-dimensional array that acquires 3D ultrasound images inside a human body.

In some embodiments, the 3D position system determines the position of the ultrasound treatment transducer 108 and the relationship of the positions between the imaging transducer 105 and ultrasound treatment transducer 108. In some embodiments, an imaging ultrasound transducer 105 may be included near the therapy module 102, such that images may be acquired of the region of the anatomical structure being targeted, tracked, and treated as will be described below.

In some embodiments, the imaging module may acquire an ultrasound image. For example the imaging module may use echoes of ultrasound pulses to delineate objects or areas of different density in the body. A frequency range used may be between 0.5 to 18 megahertz or up to 50 or 100 megahertz. Alternatively, x-ray, computed tomography, magnetic resonance, or any other type of imaging modality, optical or otherwise, may be used. In some embodiments, the imaging of an anatomical structure may be acquired in a B-mode image, Harmonic image, a color Doppler image, a color power Doppler image, a directional color power Doppler mode image, any other type of image, or any combination of two or more of the foregoing. For example, in a B-mode image and/or Harmonic image, the system may image a two-dimensional cross-section of the tissue. Alternatively or additionally, the system may utilize color Doppler imaging, an imaging technique that combines anatomical information derived using ultrasonic pulse-echo techniques with velocity information derived using ultrasonic Doppler techniques to generate color-coded maps of tissue velocity superimposed on grey-scale images of tissue anatomy. Further, color power Doppler imaging has increased intensity and the added benefit of depicting flow in small vessels.

In some embodiments, the imaging module 101 may function to identify a position of a region of an anatomical structure, such that the therapy module 102 may deliver therapy in a substantially continuous manner to the target tissue. The imaging module 101 may rapidly identify the position of the target tissue such that the therapy module 102 may then rapidly deliver therapy to the target tissue. In an interleaving pattern, the position may be identified, followed by therapy delivery, followed by position identification, and so on. This interleaving pattern of the imaging module and therapy module may occur in rapid, repetitive succession such that therapy is delivered substantially continuously. The rapid, repetitive succession is required, such that the target tissue may be tracked substantially continuously and the therapy may be delivered substantially continuously.

In some embodiments, the imaging module 101 may function rapidly, such that a dose of therapy may be delivered substantially continuously to the target tissue without significant delay between identifying a position of the target tissue and delivering therapy to the target tissue or between subsequent doses of therapy to the target tissue. For example, the imaging module 101 may identify one or more locations and/or features of the region of the anatomical structure in less than 10 seconds, 5 seconds, 3 seconds, 2 seconds, or 1 second. Alternatively, the imaging module may identify one or more locations and/or features of the region of the anatomical structure in less than 1000 milliseconds, 750 milliseconds, 500 milliseconds, 250 milliseconds, 100 milliseconds, 75 milliseconds, 50 milliseconds, 25 milliseconds, 10 milliseconds, 5 milliseconds, or 1 millisecond. In some embodiments, the imaging module may use a frame rate of greater than or equal to 20 Hz. Alternatively, the imaging module may use a frame rate of less than 20 Hz.

Returning to FIG. 1, in some embodiments, the image tracking subsystem 104 of imaging module 101 includes a tracker and a detector. Both the tracker and detector are computer algorithms configured to identify and track a shape, location, and/or feature of a region of an anatomical structure in an image by searching within a region of interest in the image for a shape, location, and/or feature of the region of the anatomical structure. As described below in further detail, the imaging module 101 may weigh results from the tracker and detector differentially, such that in some instances only the tracker results may be used, or alternatively, only the detector results or both. In some embodiments, the tracker and detector may each independently identify and track a shape, location, and/or feature of a region of an anatomical structure in an image. The tracker and detector may identify motion of a region of an anatomical structure and compensate for the motion by adjusting the focal point, such that therapy may be delivered substantially continuously to a target tissue. In some embodiments, a system may use both a tracker and detector to identify and track a region of an anatomical structure in an ultrasound image. The tracker and the detector complement each other, increase robustness of the system, and compensate for non-uniformity of ultrasound waves (as compared to imaging with light) in their interactions with an object or tissue being imaged.

In some embodiments, the tracking capabilities of the tracker and detector may be combined into one algorithm, negating the need for a separate tracker and detector. In some embodiments, results from the tracker and detector may be compared to templates, which identify a previous shape, location, and/or feature of the region of the anatomical structure. For example, the tracker may be a short-term detector in that the results are compared to several previous image ($I_{n-p}$, $I_{n-p-1}$, . . . $I_{n-3}$, $I_{n-2}$, $I_{n-1}$) and use weighted function to obtain the final position. In some embodiments, the tracker will first look for change near the previous location (i.e. previous image ($I_{n-1}$) rather than looking throughout the entire image. Further for example, the detector may be a long-term detector in that the results are compared to more than one template (i.e. a template pool) from any number of previous images. In some embodiments, the long-term template management samples breathing cycles. In general, the combination of the complimentary tracker and detector will enable the system to compensate automatically, without user intervention, if the target becomes lost or unfocused. Alternatively, any quantity and/or type of trackers and/or detectors may be used. In some embodiments, the system may include additional trackers and/or detectors such that the additional trackers and/or detectors complement the existing trackers and detectors for tracking a region of an anatomical structure. In some embodiments, the multiple complementary trackers and/or detectors may lead to an increased computation time and/or memory requirements, however the robustness of the system will also improve. In some embodiments, the system 100 further includes an integrator. The integrator is an algorithm configured to compare and/or integrate the results from tracker and detector of the image tracking subsystem of the imaging module 101 and direct the therapy module 102 to deliver the therapy to the target tissue.

Figure 2:
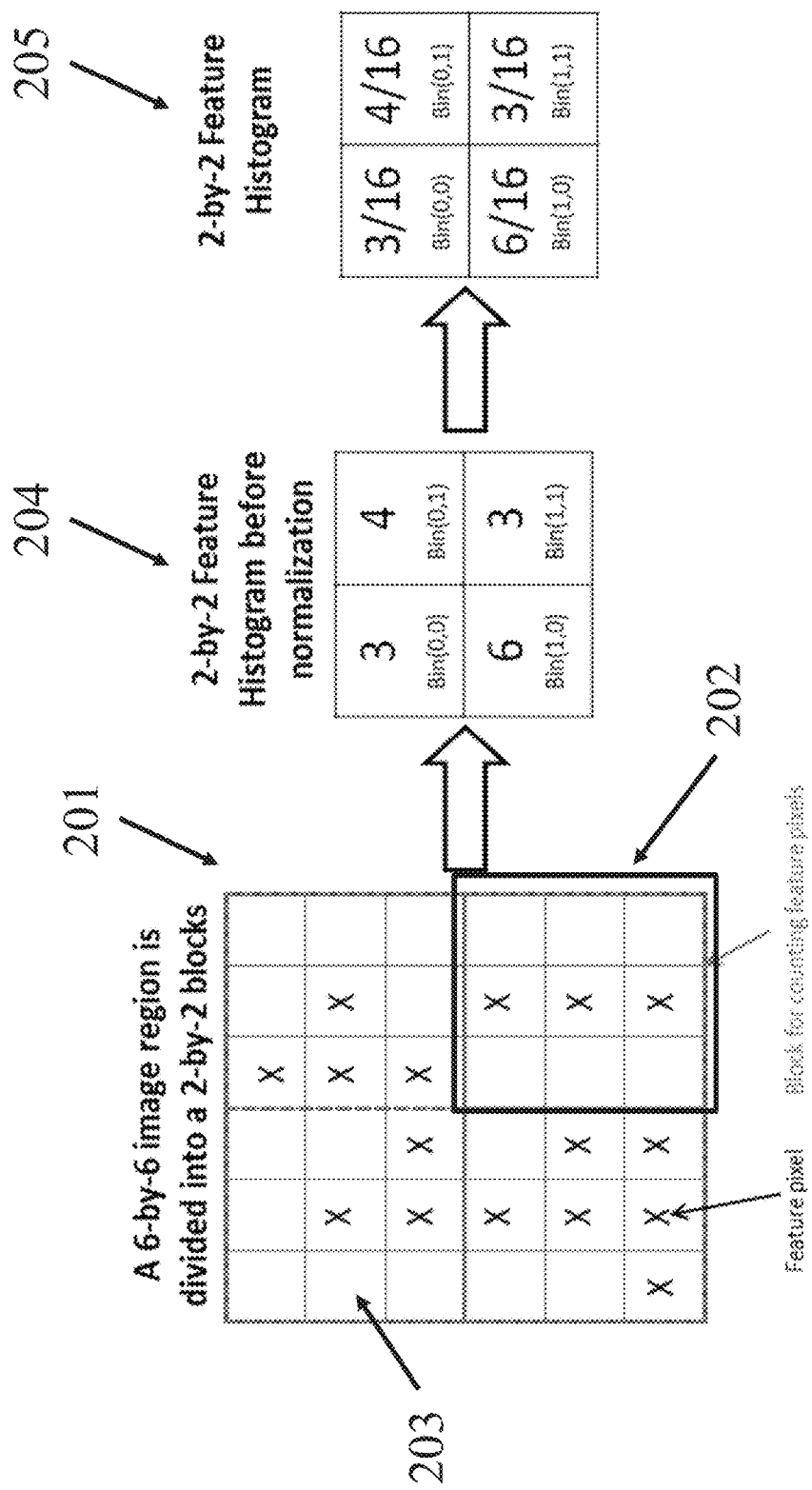
FIG. 2 illustrates a tracking algorithm, in accordance with a preferred embodiment.

The tracker and detector are algorithms for determining a location and/or feature of a region of an anatomical structure. In some embodiments, as shown in FIG. 2, a feature histogram algorithm may be used. Feature histogram describes the two-dimensional spatial distribution of the featured pixels in a defined area or analysis region 201. As shown in FIG. 2, the analysis region 201 may be equally divided into several smaller regions. The analysis region 201 containing 6 by 6 pixels, as shown in FIG. 2, is subdivided into 4 sub-regions 202, which contains 3 by 3 pixels 203. However, it should be understood that any number of pixels in analysis region 201 may be used, for example less than 36 pixels or more than 36 pixels. For example, a 5×5, 75×75, 100×100, 500×500, or 1000×1000 pixels, or anything above, below or in-between may be utilized.

In some embodiments, as shown in FIG. 2, a pixel 203 of an anatomical structure may be identified, for example by contrast, pixel density, or intensity, in the analysis region 201, denoted by an "x" in the pixel 203. Each "x" or pixel feature may be totaled for each sub-region, resulting in a 2 by 2 feature histogram 204 of region 201. The 2 by 2 feature histogram 204 is further normalized into a 2 by 2-normalized feature histogram 205. The distribution of the feature histograms indicates a location or feature of the region of the anatomical structure. However, it should be understood that any number of histogram dimension can be used, for example 4 by 4, 8 by 8, 8 by 4, 4 by 8, 16 by 16, 16 by 8, 8 by 16, 32 by 32 or any other number.

In some embodiments, a first feature histogram indicating a first location or feature of a region of an anatomical structure may be compared to second feature histogram indicating a second location or feature of the region of the anatomical structure. In some embodiments, the first or second feature histogram may include a template from a previous image. The two histograms may be compared using equation (1) below, where $H_1^{ij}$ is the first feature histogram, $H_2^{ij}$ is the second feature histogram, N is the total number of bins in the x-direction of the 2D feature histogram, M is the total number of bins in the y-direction of the 2D feature histogram, and D is the distance between the two histograms between 0 and 1. When D=0, the two histograms are identical. Conversely, when D=1, the two histograms are the most different.

$$D = \sqrt{1 - \sum_{i=1}^{N} \sum_{j=1}^{M} \sqrt{H_1^{ij} H_2^{ij}}} \quad (1)$$

In some embodiments, alternative algorithms may be employed, such as sum squared difference, sum absolute difference, or normalized cross correlation (NCC). For example, in NCC, a position of the region of the anatomical structure is determined by a pixel-wise comparison of the current image with the template containing a previous position of the region of the anatomical structure. The search region in the template is shifted in discrete steps in the N and M directions, and then the comparison is calculated (i.e. subtracting the mean and dividing by the standard deviation at every step) over the template search area for each position. The position of the maximum NCC values indicates the position of the region of the anatomical structure in the current image. Alternatively, any other threshold NCC value (i.e. minimum) may be used.

Figure 3B:
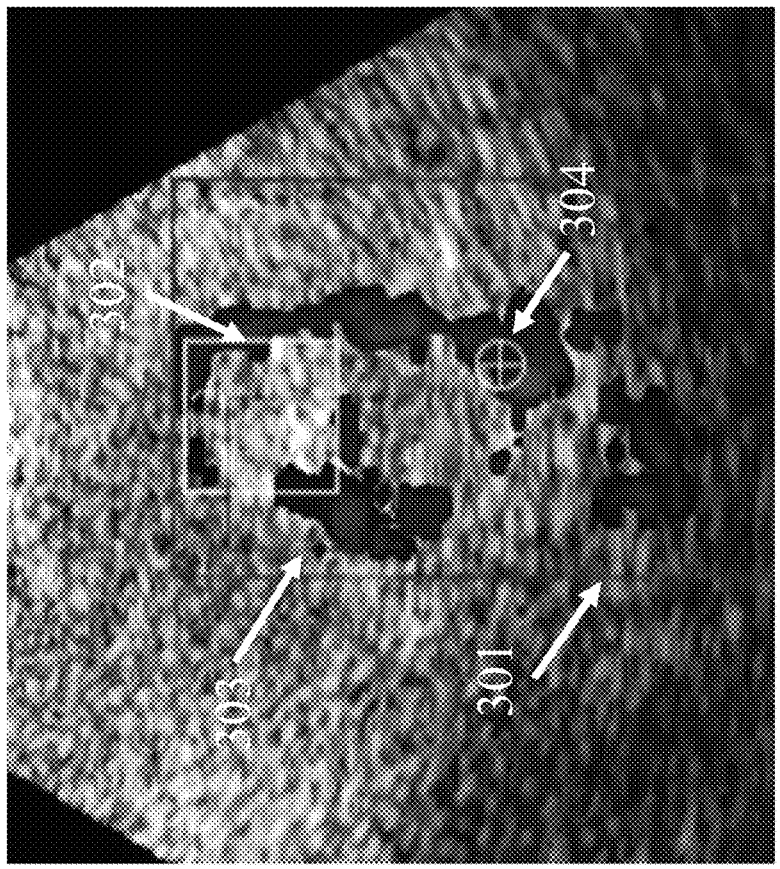
FIGS. 3A and 3B illustrate images used for tracking and delivery of therapy to a target tissue, in accordance with a preferred embodiment.
Figure 3A:
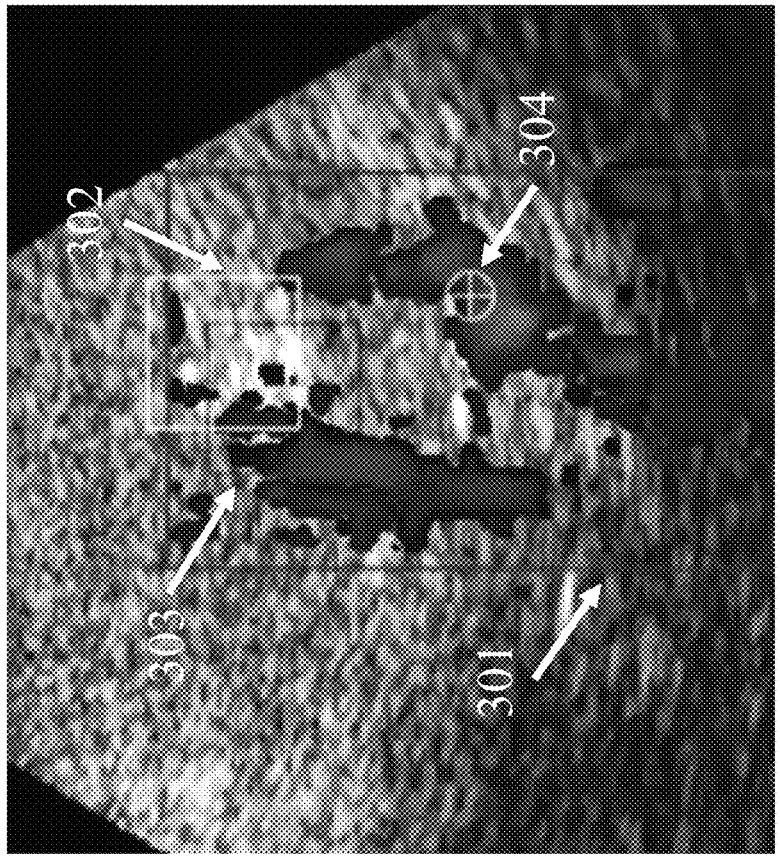

FIGS. 3A and 3B illustrate a region of an anatomical structure that is being tracked by two tracking boxes 302, 303 working on different tissue areas, in and around a region 301 that is viewable by a user. Each tracking box is associated with its own tracker, detector, and integrator. As shown in FIG. 3, two tracking boxes 302, 303 are used to increase the robustness and fidelity of the system, such that both the first and second tracking boxes are tracking a similar region of the anatomical structure in each of the tracking boxes 302, 303. Tracking is not completely lost and therapy is not stopped unless both boxes lose tracking. For example, if the first tracking box (associated with tracker, detector, and integrator) becomes lost and/or is unable to find the region of the anatomical structure, the second tracking box (associated with tracker, detector, and integrator) will continue tracking the region of the anatomical structure and therapy delivery will continue and vice versa.

In this example, the tracking boxes are tracking a location or feature of a region of an anatomical structure in two images, at opposite ends of a breathing cycle, using a feature histogram algorithm, as described above. For example, a beginning of a breathing cycle is shown in FIG. 3A and an end of a breathing cycle is shown in FIG. 3B. The crosshairs 304 indicate a target region or tissue for receiving therapy. As shown in FIG. 3, the target tissue (e.g. renal artery) receiving therapy is distinct from the regions of the anatomical structure (e.g. tissue) that is being tracked by the tracking boxes. In some embodiments, the search region may be any size, for example 361 pixels by 420 pixels. Alternatively, the search region may be larger than 361 pixels by 420 pixels or less than 361 pixels by 420 pixels. The tracking boxes 302, 303 may be any size, for example 64×64 pixels. Alternatively, the tracking boxes may be less than 64×64 pixels or greater than 64×64 pixels. In some embodiments, a user may select the tracking box size. Alternatively, the tracking box size may be selected automatically by the system. Alternatively, only one tracking box or more than two tracking boxes may be used. In some embodiments, the system may include additional tracking boxes to add redundancy to the system. In some embodiments, the multiple complementary trackers and/or detectors may lead to an increased computation time and/or memory requirements, however the robustness of the system will also improve.

In some embodiments, the tracking performed by the first and second tracking boxes may occur with an accuracy of root-mean-square (RMS) error of less than or equal to 2 mm. Alternatively, the RMS error may be more than 2 mm, but still within a suitable accuracy. In some embodiments where two tracking boxes are used, if both the tracking boxes 302, 303 are lost, the tracking boxes 302, 303 may recover at the same time and maintain the same relative position with error within less than or equal to 40 pixels. Alternatively, the error may be within more than 40 pixels. Further, in some embodiments, if the region of the anatomical structure moves outside of the image, the tracker and detector will cease to track the region of the anatomical structure.

In some embodiments, as shown in FIG. 4, a tracker may function as a short-term detector, as described above. The tracker may compare a feature histogram of a current location or feature of a region of an anatomical structure in a current image ($I_n$) to a template. In some embodiments, the template may be a feature histogram of a previous location or feature of the region of the anatomical structure in a previous image ($I_{n-1}$). In some embodiments, the tracker may search for a change in a region of the anatomical structure near a previous location of the region of the anatomical structure in the template instead of searching an entire template. The two feature histograms are compared, for example using equation (1), and the minimum distance D between the two feature histograms may be determined and the x, y coordinates of the point of the minimum distance D may be identified, as shown in FIG. 4. Alternatively, a maximum distance D or any other threshold may be used when comparing two or more feature histograms.

Figure 5:
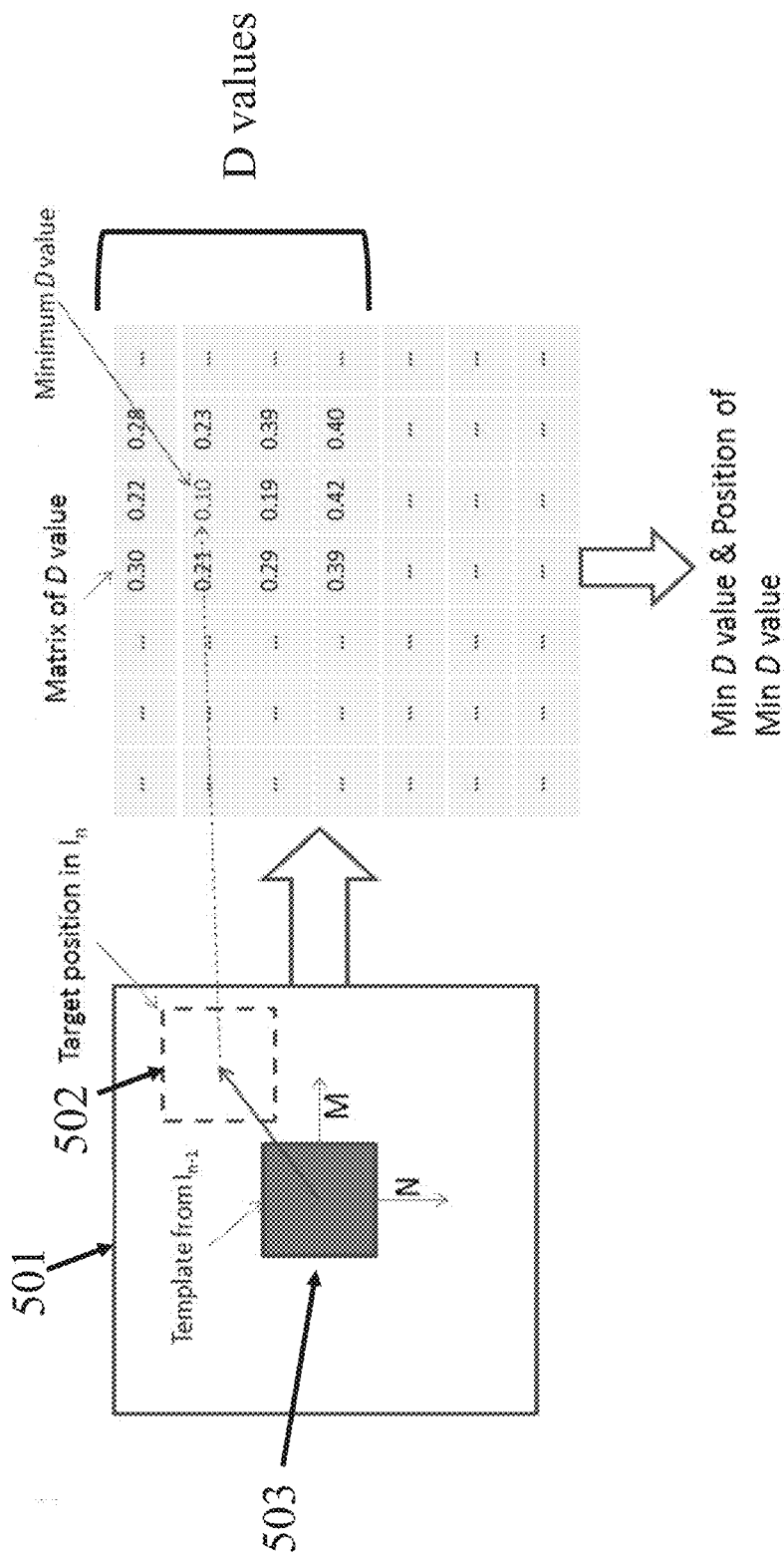
FIG. 5 illustrates a tracker algorithm, in accordance with a preferred embodiment.

As shown in FIG. 5, within the search region 501, the tracker tracks a possible current location or feature 502 of a region of the anatomical structure in the current image ($I_n$). The previous location or feature (with M, N coordinates) of the region of the anatomical structure from image ($I_{n-1}$) is a template 503, as described above. In some embodiments, the tracker may search for a change in a region of the anatomical structure near a previous location of the region of the anatomical structure instead of searching the entire image. The distance between the feature histograms of the possible current location or feature 502 and the previous location or feature 503 of the region of the anatomical structure is calculated. Each of the distances may be represented by value D, such that the minimum D value and the position of the minimum D value indicate a best match between a current location or feature and a previous location or feature of the region of the anatomical structure in the template.

Figure 6:
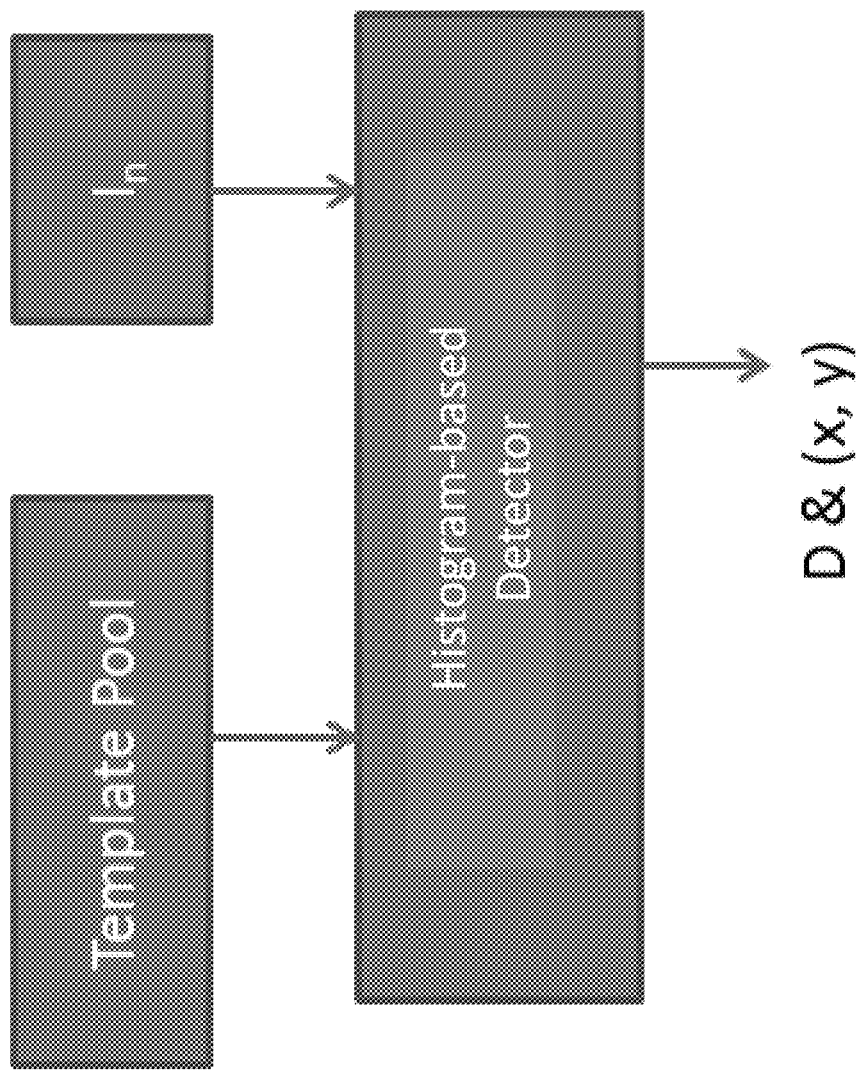
FIG. 6 illustrates a flow chart for the functioning of a detector, in accordance with a preferred embodiment.
Figure 7:
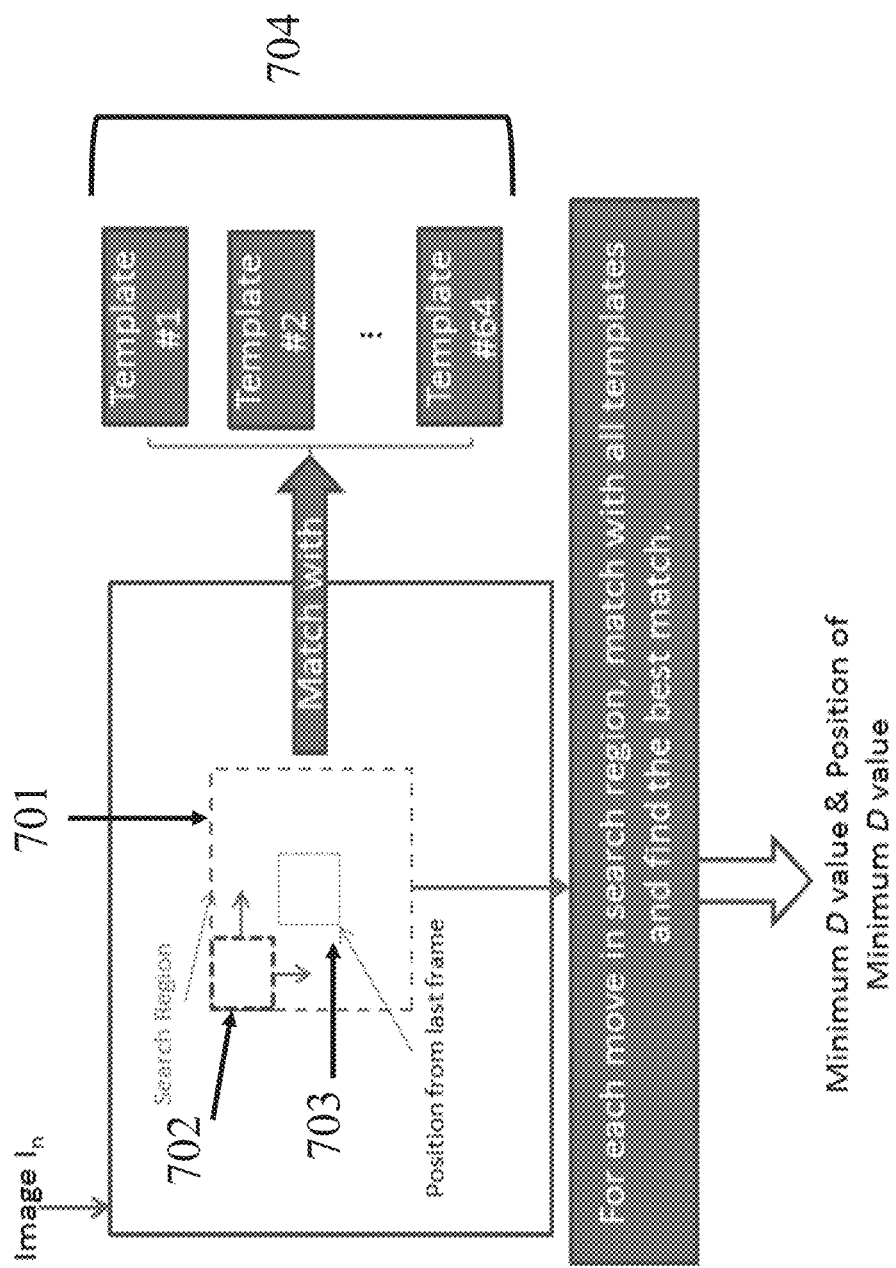
FIG. 7 illustrates a detector algorithm, in accordance with a preferred embodiment.

As shown in FIGS. 6 and 7, within the search region 701, the detector may function as a long-term detector, as described above. The detector may detect a possible current location or feature of a region of the anatomical structure in a current image ($I_n$). The feature histogram of the possible current location or feature 702 in a current image $I_n$ is compared to a template pool 704 comprising feature histograms for one or more templates of previous locations and/or features, for example 703, of the region of the anatomical structure in previous images ($I_{n-1}$). For example, a template pool 704 may include a plurality of templates. As one example, the template pool 704 may include 64 templates. The feature histograms of the possible current location or feature 702 of a region of the anatomical structure are compared to the feature histograms of the one or more templates, for example 703, through calculating the D value. The template corresponding to the minimum D value and the position of the minimum D value indicates a best match between a current location or feature 702 and the template from the template pool 704, identifying the location or feature as the region of the anatomical structure 701, as shown in FIG. 7. In some embodiments, a maximum Normalized Cross Correlation (NCC) value may correspond to a best match between a current location or feature and the template from the template pool, which could replace the D value as described above.

In some embodiments, the feature histogram of the current image is compared to all templates in the template pool. Alternatively, the feature histogram of the current image may be compared to a subset of the template pool. In some embodiments, all templates search in their own search regions and the region of the anatomical structure is at the position, which gives the maximum (i.e. NCC value) or minimum value (i.e. sum squared difference value) in all search regions of the templates.

Figure 8:
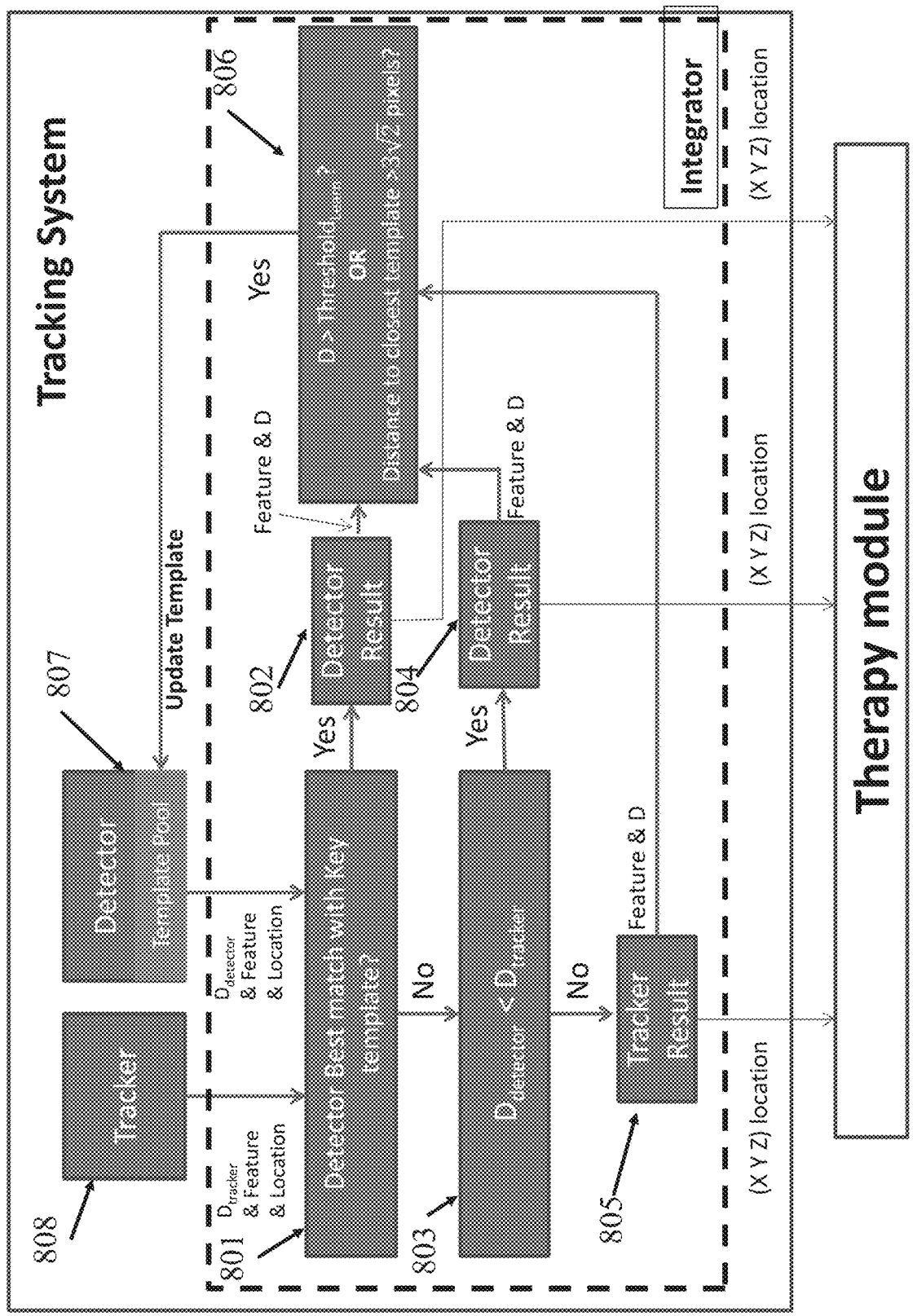
FIG. 8 illustrates a flow chart for the functioning of an integrator, in accordance with a preferred embodiment.

FIG. 8 illustrates an integrator flow chart. In some embodiments, as shown in FIG. 8, an integrator is an algorithm that compares the tracking results from the tracker and detector and determines (1) if the results from the tracker or detector should be used in determining a current location or feature of the region of the anatomical structure and (2) if the results from the tracker and detector should be added as a template to the template pool. In some embodiments, the integrator weighs the results of the detector more heavily. As shown in FIG. 8, if the results from the detector match with a key template, which is a template sampled throughout the motion cycles, then the integrator will use the detector results 802. Otherwise, if the distance value D determined by the detector is less than the distance value D determined by the tracker 803, the integrator will use the results from the detector 804, such that the smaller distance value D from the detector more accurately defines the feature histogram of the location or feature. Alternatively, if the distance value D determined by the detector is more than the distance value D determine by the tracker, then the integrator further evaluates the results from the tracker 805. If the distance value D is greater than a predetermined threshold or if the distance of the current location to the closest template location is greater than a predefined pixel distance (L), for example $3\sqrt{2}$ or any other distance, the feature histogram denoted by distance value D will be updated as a template and maintained as part of the template pool 807. In some embodiments, if the location of a current feature is a predefined distance (L) from all other templates in the pool, then the current feature will be saved as a "key" template. Any of the above integrations performed by the integrator may be sent to the therapy module, such that an x, y, z coordinate of the current location may be sent to the therapy module and the therapy module may deliver therapy to the target tissue, as shown in FIG. 8. In some embodiments, the time between the therapy module receiving instructions and delivering therapy is less than or equal to 50, 40, 30, 20, 10, 5, or 1 milliseconds. Alternatively, the time between receiving instructions and delivering therapy may be more than 50 milliseconds.

In some embodiments, as shown in FIG. 9A, a system 900 for tracking a region of an anatomical structure and delivering therapy to a target tissue may further include a filter 901. The filter may use an algorithm to reduce noise in the image ($I_n$), such that the imaging module 902 may determine one or more locations and/or features of the region of the anatomical structure in the image ($I_n$). In some embodiments, the noise may include speckle, multiple coherent reflections from the environment surrounding the region of the anatomical structure or target tissue, or any other type of noise. In some embodiments, the filtered image may be visible only to one of the tracker or detector. Alternatively, both the tracker and detector may use the filtered image. In some embodiments, a user of the system 900 may select between viewing the filtered image or an unfiltered image.

In some embodiments, as shown in FIG. 9B, a filter may use a simple moving average filter to remove noise in an image ($I_n$). As shown in FIG. 9B, each region 903 of the image may be identified ($i_n$) and the average intensity of the pixels in each region may be determined. Equation (2) may be used to smooth the image, such that y[i] equals the smoothed pixel intensity, M equals the number of regions 903 in the average, i equals the location of smoothed pixel, and j equals the index within the region. Alternatively, any other type of filtering equation may be used.

$$y[i] = \frac{1}{M} \sum_{j=0}^{M-1} x[i*j] \quad (2)$$

Figure 10:
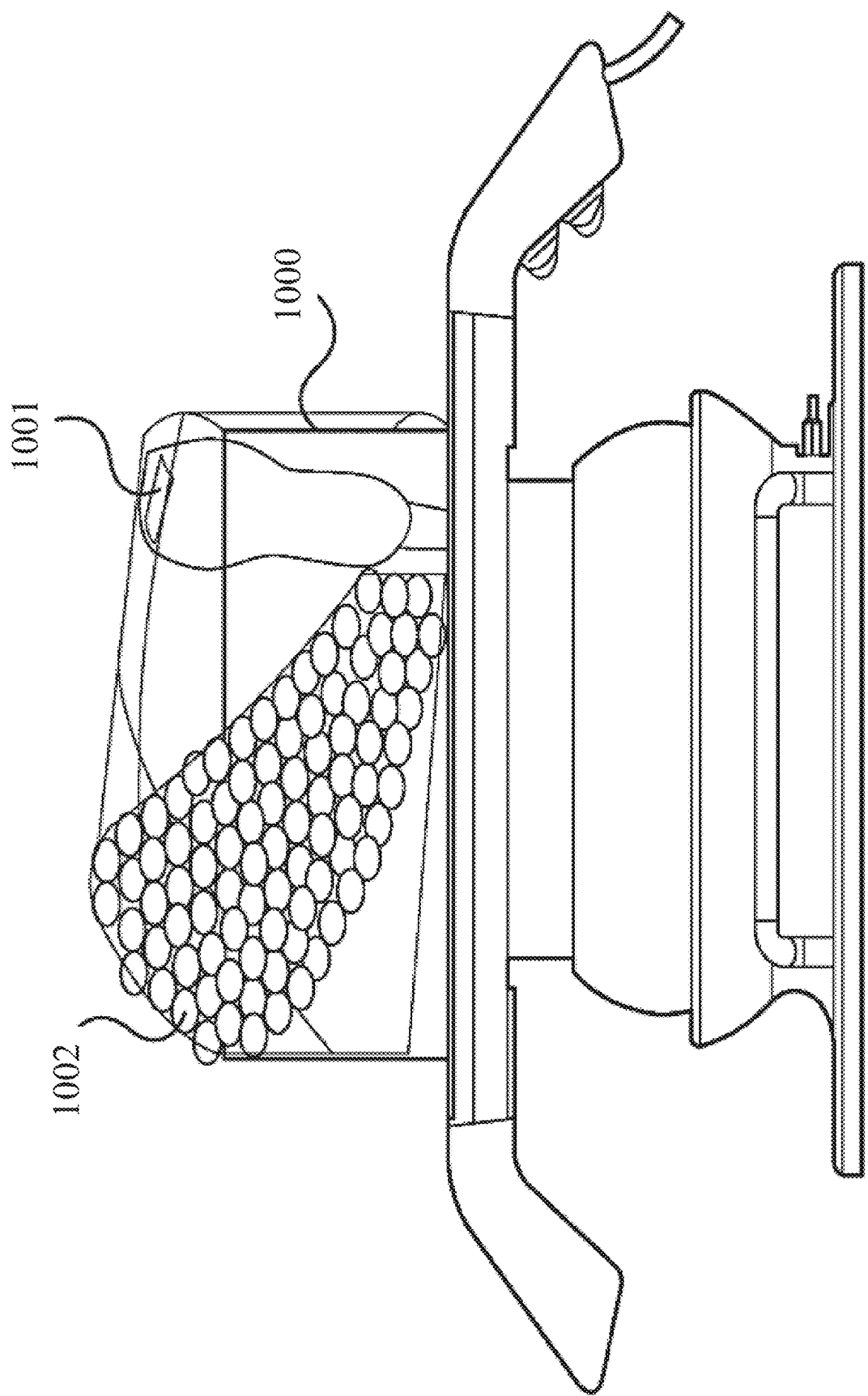
FIG. 10 illustrates a therapy module, in accordance with a preferred embodiment.
Figure 11:
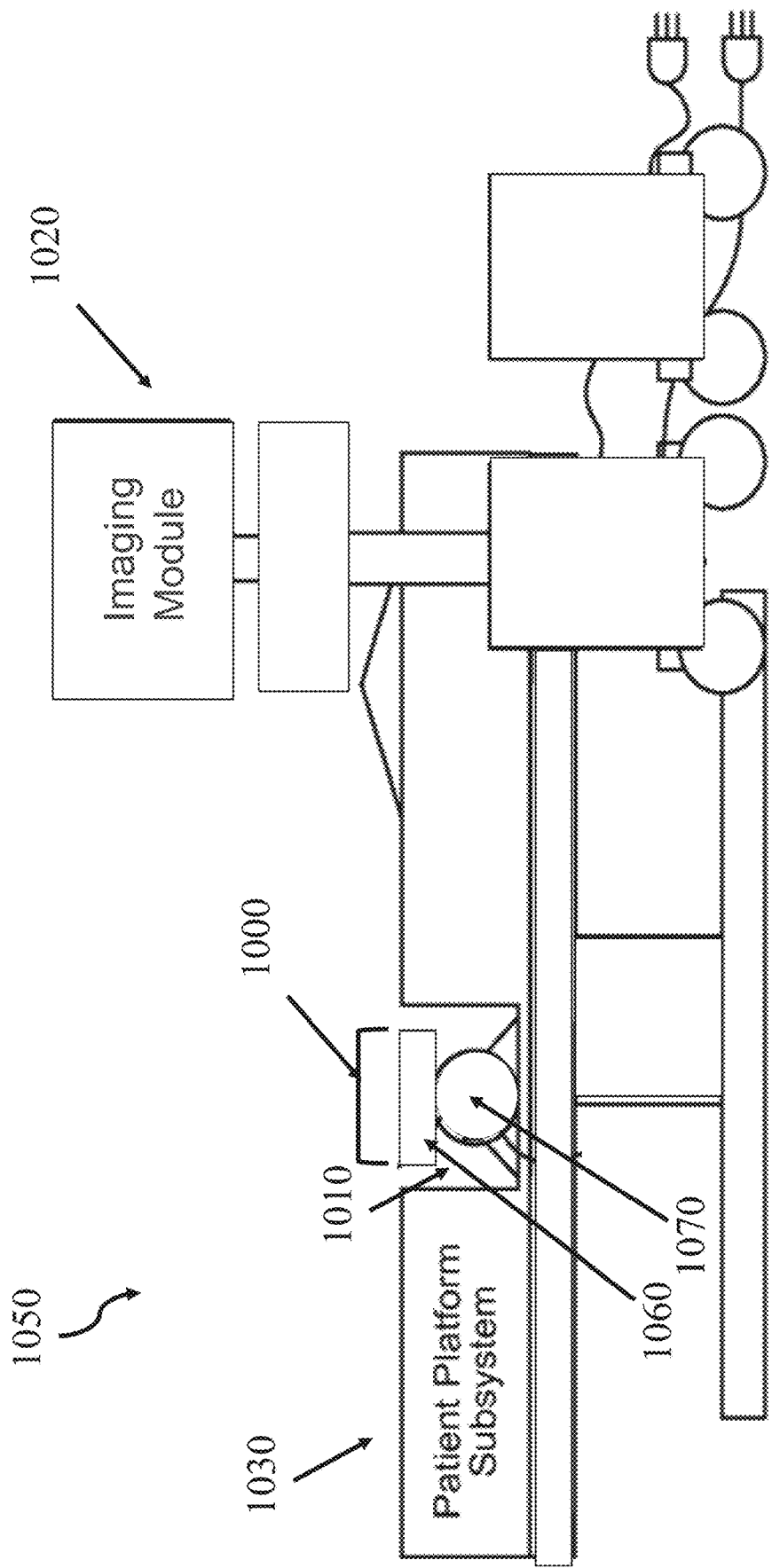
FIG. 11 illustrates a system including an imaging and therapy module, in accordance with a preferred embodiment.

In some embodiments, where the integrator integrated the results from the tracker and detector, as described above with respect to FIG. 8, the therapy module may receive a current target tissue location and a distance to the current target tissue location from the integrator. In some embodiments, the therapy module 1000 may include one or more ultrasound transducers 1001, 1002, as shown in FIG. 10. The therapy module 1000 may include a phased or fixed array of ultrasound transducers 1002 for delivering therapy to the target tissue. Further, in some embodiments, as shown in FIG. 10, the therapy module may include a second phased or fixed array of ultrasound transducers 1001 for acquiring images of the region of the anatomical structure. The region of the anatomical structure may then be tracked in the image by the tracker and detector, as described above. As shown in FIG. 11, the therapy module 1000 may be integrated into a patient platform 1030, such that the therapy module 1000 is positioned in a cavity 1010 of the patient platform 1030 while maintaining access to a patient lying on the patient platform 1030. In some embodiments, the imaging module 1020 may be in the same room and/or electrically connected to the patient platform 1030 and/or the therapy module 1000. Alternatively, the imaging module 1020 may be in communication with the therapy module 1000 through Bluetooth, Wi-Fi, or any other type of connection. Other features and aspects of the system 1050 of FIG. 11 are disclosed in PCT Application Serial Number 2014/022141, which is herein incorporated by reference.

In some embodiments, the ultrasound transducer of the therapy module may be moved, repositioned, or otherwise relocated by a motion control mechanism. Alternatively, the ultrasound transducer of the therapy module may be directed and moved to guide therapeutic energy to the target tissue, for example by an applicator 1060. In some embodiments, the ultrasound transducer of the therapy module may be moved by a three-dimensional electronic beam steering control mechanism to guide therapeutic energy to the target tissue. Alternatively, the ultrasound transducer of the therapy module may be moved by a mechanical control mechanism to guide therapeutic energy to the target tissue.

Figure 12A:
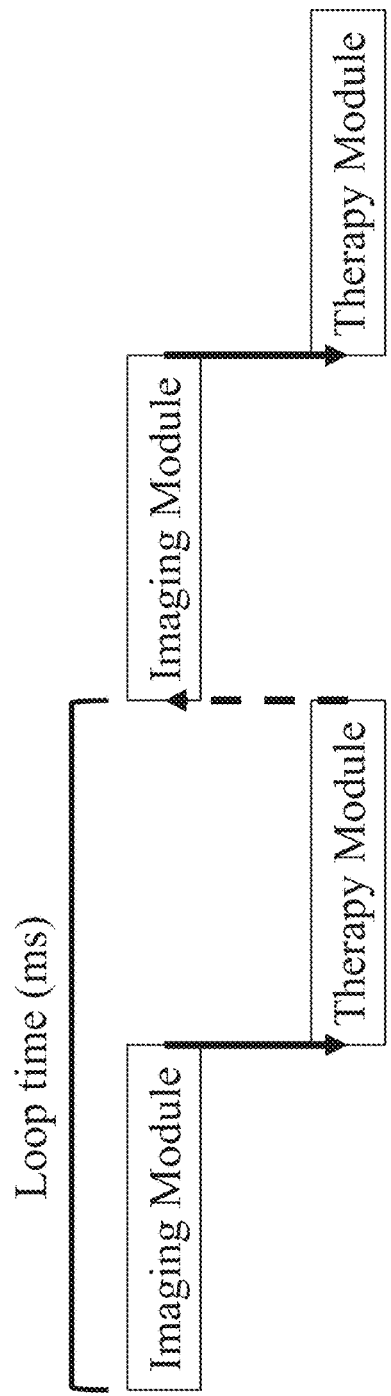
FIGS. 12A and 12B illustrate an interleaving and a continuous mechanism for imaging and therapy delivery, respectively, in accordance with first and second preferred embodiments.
Figure 12B:
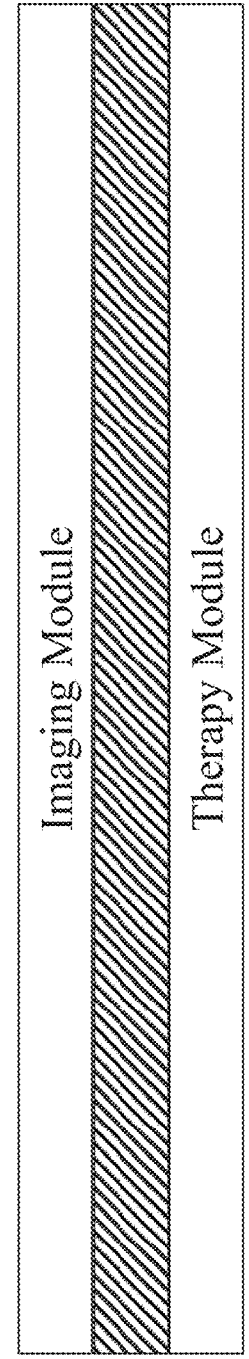

In some embodiments, as shown in FIG. 12A, the imaging module and therapy module may function in rapid succession in an interleaving mechanism. FIG. 12A illustrates the interleaving pattern with solid arrows representing hard sync triggers and dashed arrows representing soft sync triggers. The interleaving pattern, as shown in FIG. 12A, may continue until the prescribed dose of therapy has been delivered. In some embodiments, the therapy module will be re-targeted to a new lesion or position and the interleaving mechanism will resume. Alternatively, in some embodiments, the imaging module and therapy module may function simultaneously, such that therapy is continuously being delivered while the imaging module is transmitting tracker and detector results to the therapy module, as shown in FIG. 12B. Alternatively or additionally, the therapy module may function using a predictive mechanism, such that the therapy module may predict a future position of the region of the anatomical structure that is being tracked by the imaging module from several previous target positions and move to that predicated position to deliver therapy.

Figure 13:
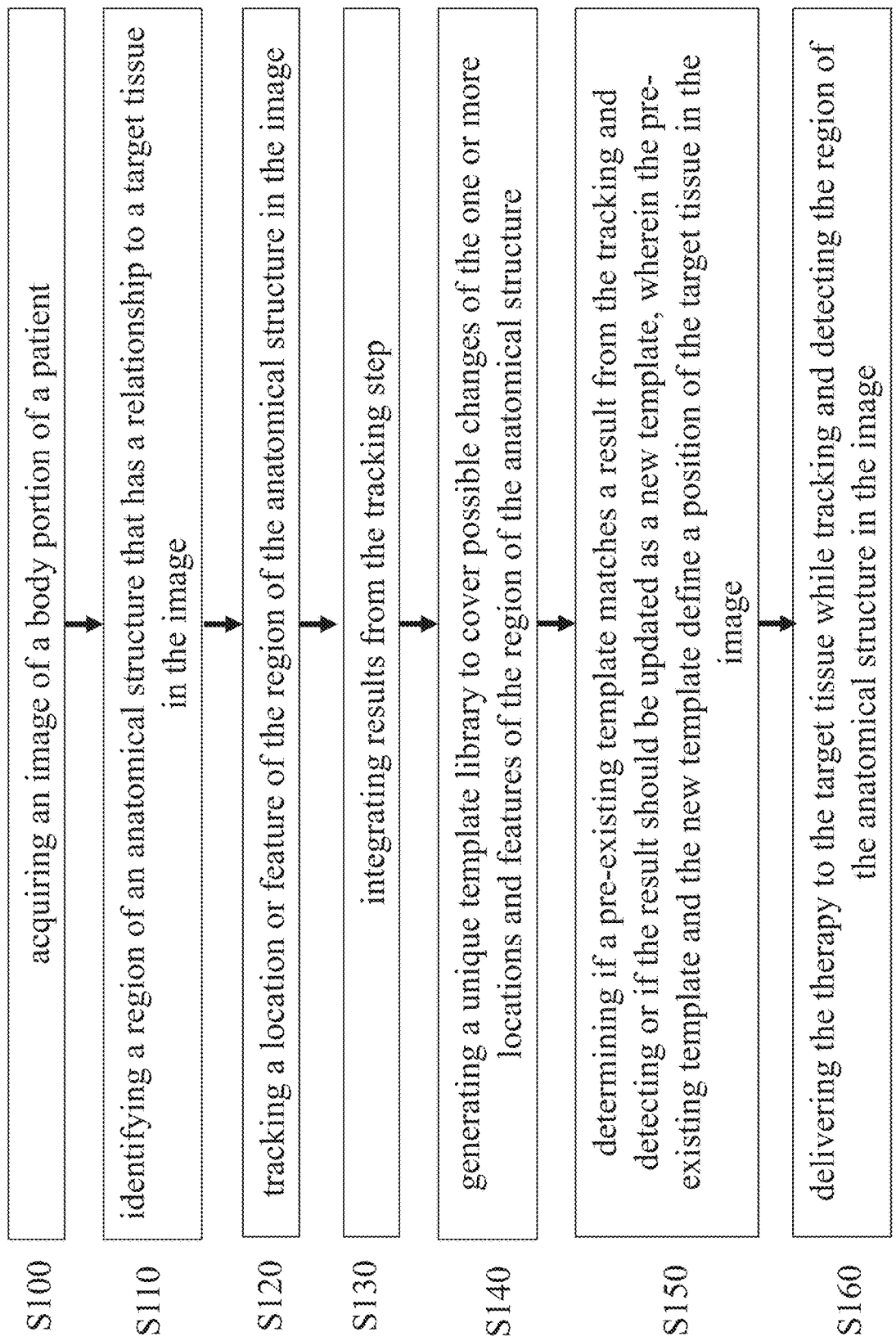
FIG. 13 illustrates a method of tracking a target tissue and delivering therapy to a target tissue, in accordance with a preferred embodiment.

FIG. 13 illustrates a method of tracking a target tissue and delivering therapy to a target tissue, in accordance with a preferred embodiment. As shown in FIG. 13, a method for imaging during delivery of a therapy of a preferred embodiment includes the steps of acquiring an image of a body portion of a patient S100; identifying a region of an anatomical structure that has a relationship to a target tissue in the image S110; tracking a location or feature of the region of the anatomical structure in the image S120; integrating the results from the tracking S130; generating a unique template library to cover possible changes of the one or more locations and features of the region of the anatomical structure S140; determining if a pre-existing template matches a result from the tracking or if the result should be updated as a new template, wherein the pre-existing template and the new template define a position of the target tissue in the image S150; and delivering the therapy to the target tissue while tracking the region of the anatomical structure in the image S160. In some embodiments, the method preferably functions to track a region of an anatomical structure, such that the position of the anatomical structure correlates with a position of a target tissue. The method may be used for delivering ultrasound to denervate a renal artery but, additionally or alternatively, can be used for any suitable applications, clinical or otherwise. For example, the method may be used to deliver ultrasound to a kidney, gallbladder, bile duct, or ureter to disrupt kidney, gallstones, bile duct stones, or ureter stones, respectively.

As shown in FIG. 13, step S100 includes acquiring an image of a body portion of a patient. Step S100 preferably functions to image a region of an anatomical structure of a patient, such that a location and/or feature of a region of the anatomical structure may correspond to a position of the target tissue for receiving therapy. As described above, the image may be acquired in B-mode, Harmonic image, color Doppler, color power Doppler, or directional color power Doppler mode image. In some embodiments, the imaging may be performed using ultrasound or any other type of imaging modality, optical or otherwise.

As shown in FIG. 13, step S110 includes identifying a region of an anatomical structure that has a relationship to a target tissue in the image. Step S110 preferably functions to identify a region of an anatomical structure that moves, deforms, or otherwise tracks in a similar manner as the target tissue, such that the anatomical structure may be tracked while the target tissue is receiving therapy. For example, if the target tissue moves 2 cm to the right in the image, the region of the anatomical structure being tracked should also move 2 cm to the right. In some embodiments, the target tissue is the anatomical structure being tracked.

As shown in FIG. 13, step S120 includes tracking a location or feature of the region of the anatomical structure in the image. Step S120 preferably functions to track a location or feature of a region of the anatomical structure using a tracker and detector, such that the therapy module may be notified of a change in location or feature of the target tissue. In some embodiments, step S120 occurs in response to a change in location or feature of the region of the anatomical structure.

As shown in FIG. 13, step S130 includes integrating the results from the tracking with the tracker and detector. Step S130 preferably functions to determine if the results from the tracker and detector will be used and if a new template should be generated based on the results from the tracker and detector. For example, if the tracking results from the tracker and detector, respectively, match a key template, as described above, the integrator will use the detector results and instruct the therapy module to deliver therapy to the target tissue, such that a position of the target tissue is known by the integrator and transmitted to the therapy module.

As shown in FIG. 13, step S140 includes generating a unique template library to cover possible changes of the one or more locations and features of the region of the anatomical structure. Step S140 preferably functions to maintain a template pool of possible locations and/or features of the anatomical structure being tracked by the imaging module, such that the template pool was generated over time from previous images. Each result from the tracker and detector may be compared to the template pool to determine if 1) the result matches a template and thus the template can inform the therapy module as to the position of the target tissue or 2) the result does not match a template and a new template needs to be generated and thus the new template can inform the therapy module as to the position of the target tissue, as further recited in S150.

As shown in FIG. 13, step S160 includes delivering the therapy to the target tissue while tracking the region of the anatomical structure in the image. Step S160 preferably functions to deliver therapy to the target tissue while consistently aligning an orientation, position, or otherwise direction of the therapy module with the target tissue. The therapy module, as described herein, receives information from the imaging module that pertains to a position of the target tissue, such that the tracker and detector track a position of the target tissue by tracking a region of an anatomical structure.

In some embodiments, the method of FIG. 13 further includes substantially continuously delivering therapy to the target tissue despite a change in one or more locations and features of the region of the anatomical structure. The therapy module may continue delivering therapy despite a change since the imaging module may alert, notify, or otherwise inform the therapy module of the change, and the therapy module may adjust accordingly.

In some embodiments, the method of FIG. 13 further includes stopping the imaging of the region of the anatomical structure when the region of the anatomical structure is undetectable. For example, the anatomical structure may move perpendicularly away from the imaging plane, such that the region of the anatomical structure is undetectable. In some embodiments, the imaging module may automatically recover (e.g. without user intervention) the region of the anatomical structure location or feature, such that therapy delivery may resume. Further, automatically recovering the region of the anatomical structure location or feature may occur by first determining a last known location or feature of the region of the anatomical structure in the image (logic function). In some embodiments, the last known location or feature may correspond to a template from the template pool.

In some embodiments, the method of FIG. 13 further includes filtering the image, such that the anatomical structure can be tracked in the filtered image. The image may be filtered using a moving average filter or any other type of filter.

In some embodiments, the method of FIG. 13 further includes generating a new template when the pre-existing template does not match the tracking results, such that the new template corresponds to a position of the target tissue in the image. In some embodiments, the new template is assigned as the key template, as described above. In some embodiments, the new template may be generated by the integrator.

In some embodiments, the method of FIG. 13 is implemented in a graphics processing unit (GPU), FPGA, and/or DSP to further reduce the computation time of the tracker, detector and integrator.

As described herein, a method for treatment includes: acquiring with an imaging module an image of a body portion of a patient; identifying a region of an anatomical structure that has a relationship to a target tissue in the image; tracking a location and/or a feature of the region of the anatomical structure in the image; transforming a target position of the target tissue from an imaging space associated with the imaging module to a treatment space associated with a therapy module through one or more position sensors and a transmitter; and delivering a therapy with the therapy module to the target tissue while tracking the region of the anatomical structure. In some embodiments, the act of transforming is performed to bring a target position of the target tissue (e.g., renal artery) in the imaging space (e.g., ultrasound imaging coordinate) to a transformed target position in the treatment space (e.g., therapeutic array coordinate). Various techniques may be employed to achieve such objective. For example, in some cases, a real-time electromagnetic tracking system with sub-millimeter and sub-degree accuracy may be used. The magnetic field sensor may be attached on the handle of the imaging transducer, and a magnetic field transmitter may be attached to the base of therapeutic treatment module. The magnetic field transmitter generates a magnetic field. When the magnetic sensor is placed inside controlled, varying magnetic fields generated from the transmitter, voltage are induced in the sensor coils. These induced voltages can be used by the measurement system to calculate the position and the orientation of the magnetic field sensor in 3D space. In such cases, after the renal artery target position is detected by ultrasound imaging (in image coordinate), the transformation of the position may be performed as follows: 1) the treatment position and orientation of a target in the image coordinate are linked with the magnetic field sensor position and orientation based on mechanical design and calibration (in magnetic sensor coordinate); 2) the target position and orientation in the magnetic sensor coordinate are then transformed into the treatment module coordinate by the detection of the sensor position and orientation in the magnetic field generated by the magnetic field transmitter, and 3) the target position and orientation in the treatment module coordinate are further transformed into the coordinate of the therapeutic array. In some cases, the third transformation above is not needed if the coordinate frame of the therapeutic array is aligned with the treatment module coordinate frame. Therefore, knowing the position and orientation of the imaged target relative to the coordinate frame of the therapeutic array through the above transformations, the therapeutic system can adjust the mechanical movement of the therapeutic array and/or the phases of the array elements to deliver the ultrasound energy at the imaged treatment target.

In other embodiments, non-magnetic position measurement system may be used. This has the advantage of eliminating the possibilities of wrong targeting when a metal object gets close to the magnetic sensor and the transmitter. For example, in other embodiments, optical position measurement system may be used that measures the 3D positions of either active or passive markers affixed to application-specific tools. In one implementation, three different optical tool plates with at least three optical markers on each plate may be provided. One plate with optical markers is attached with the handle of the imaging transducer. The other two plates are attached on the left and right sides of the therapeutic treatment module separately. An optical position sensor system may be attached to the base of therapeutic treatment module. The optical position sensor system emits infrared (IR) light from its illuminators, similar to the flash on a conventional camera. The emitted IR light reflects back to the Position Sensor off markers (which may be spherical or semi-spherical) on the passive tool plates. The optical position sensor system then measures the positions of the markers and calculates the positions and orientations of the tool plates. The relationship of both positions and orientations between the tool plate attached to the imaging transducer (e.g., the handle) and the treatment module can be determined by the position sensor system at a rate of 20 Hz in real-time. To further optimize the detection accuracy of the positions and orientations between the imaging transducer and treatment module, the two plates which are attached along the left and right side of the treatment module are orientated to the optimized angles for treating the right and left renal denervation separately. In such cases, after the renal artery target position is detected by ultrasound imaging (in image coordinate), the transformation of the positions and orientations of the treatment target from the imaging coordinate to the therapy coordinate may be performed as follows: 1) the target position and orientation in the image coordinate are linked with the optical plate position (of the imaging transducer) based on mechanical design and calibration (to obtain treatment position and orientation in imaging tool plate coordinate); 2) the target position and orientation in the imaging tool plate coordinate are further transformed into optical position sensor coordinate frame; 3) the target position and orientation in the position sensor coordinate frame are then transformed into either left or right tool plate coordinate frame attached on the treatment module depending on the treatment of right or left side renal nerves; 4) the target position and orientation in the left/right treatment tool plate coordinate frame are further transformed to the therapeutic array coordinate frame based on mechanical design dimension and calibrations. Thus, the therapeutic system may control the therapeutic array to deliver the ultrasound energy to the treatment target through the above transformations by adjusting the mechanical movement of the therapeutic array and/or electronic phasing steering (e.g., in depth direction, and/or other direction(s)).

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the imaging module and/or the therapy module. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, for example Versatile Data Acquisition System (VDAS), but any suitable dedicated hardware or hardware/firmware combination can alternatively or additionally execute the instructions.

In other embodiments, instead of or in addition to using histogram(s), a feature matching technique such as Normalized Cross Correlation method, Sum Square Difference method, Sum Absolute Difference method, etc., may be used.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for imaging during delivery of a therapy, the method comprising:
    acquiring an image of a body portion of a patient;
    identifying a region of an anatomical structure that has a relationship to a target tissue in the image;
    tracking at least one of a location and a feature of the region of the anatomical structure in the image;
    generating a template library comprising a plurality of templates identifying at least one of a prior location and a prior feature of the region of the anatomical structure;
    comparing results of the tracking with at least one template in the template library to determine a degree of mismatch between the results of tracking and a template from the at least one template;
    determining whether the degree of mismatch is within a threshold value;
    in response to determining that the degree of mismatch is within the threshold value, obtaining position information of the target tissue from the template; and
    delivering the therapy to the target tissue using the position information while continuing tracking the region of the anatomical structure in the image.

2. The method of claim 1, further comprising continuously delivering therapy to the target tissue despite a change in one or more locations and features of the region of the anatomical structure.

3. The method of claim 1, wherein the tracking occurs in response to a change in the location or the feature of the region of the anatomical structure.

4. The method of claim 1, wherein the region of the anatomical structure comprises the target tissue.

5. The method of claim 1, wherein at least one of breathing, blood flow, conscious movement, or unconscious movement of the patient changes at least one of the location and the feature of the region of the anatomical structure.

6. The method of claim 1, wherein the region of the anatomical structure is undetectable by an imaging module as a result of at least one of breathing, blood flow, conscious movement, and unconscious movement.

7. The method of claim 6, further comprising stopping imaging of the body portion of the patient when the region of the anatomical structure is undetectable.

8. The method of claim 7, further comprising automatically re-detecting at least one of the location and feature of the region of the anatomical structure.

9. The method of claim 8, wherein the automatically re-detecting step further comprises automatically re-detecting at least one of the location and feature of the region of the anatomical structure by first determining a last known location or feature of the region of the anatomical structure in the image.

10. The method of claim 1, wherein the tracking occurs in less than 5 milliseconds.

11. The method of claim 1, wherein the delivering the therapy comprises denervating renal nerves surrounding a renal artery.

12. The method of claim 1, wherein the delivering comprises delivering ultrasound to the target tissue.

13. The method of claim 1, wherein the tracking comprises using a B-mode image, Harmonic image, or 3D Ultrasound imaging.

14. The method of claim 1, wherein the tracking comprises using a color Doppler image, a color power Doppler image, or a directional color power Doppler mode image.

15. The method of claim 1, wherein the tracking comprises using at least one of an image in B-mode, Harmonic mode, color Doppler mode, color power Doppler mode, or a combination of the B-mode, the Harmonic mode and the color Doppler mode.

16. The method of claim 1, further comprising filtering the image to obtain a filtered image, such that the anatomical structure can be tracked in the filtered image.

17. The method of claim 1, further comprising determining if a preexisting template matches a result from the tracking.

18. The method of claim 17, wherein a position of the target tissue is based on the preexisting template and a new template.

19. The method of claim 1, further comprising determining if a result from the tracking should be updated as a new template.

20. The method of claim 1, further comprising generating a new template when a preexisting template does not match a result from the tracking, wherein the new template defines or indicates a location and a shape of the target tissue.

21. The method of claim 1, wherein delivering the therapy to the target tissue comprises delivering ultrasound for drug delivery to the target tissue.

22. A method for treatment comprising:
acquiring with an imaging module an image of a body portion of a patient;
identifying a region of an anatomical structure that has a relationship to a target tissue in the image;
tracking at least one of a location and a feature of the region of the anatomical structure in the image;
transforming a target position of the target tissue from an imaging space associated with the imaging module to a treatment space associated with a therapy module through one or more position sensors and a transmitter;
generating a template library comprising a plurality of templates identifying at least one of a prior location and a prior feature of the region of the anatomical structure;
comparing results of the tracking with at least one template in the template library to determine a degree of mismatch between the results of tracking and a template from the at least one template;
determining whether the degree of mismatch is within a threshold value;
in response to identifying determining that the degree of mismatch is within the threshold value, obtaining position information of the target tissue from the template; and
delivering a therapy with the therapy module to the target tissue using the position information while continuing tracking the region of the anatomical structure.

23. The method of claim 22, wherein the one or more position sensors and the transmitter are configured to link a position of an imaging transducer of the imaging module to a position of an ultrasound treatment transducer of the therapy module.

24. The method of claim 22, wherein the one or more position sensors comprises a magnetic sensor, an optical sensor, an ultrasound sensor, or a mechanical position sensor.

25. The method of claim 22, wherein the one or more position sensors are mounted on an imaging transducer of the imaging module.

26. The method of claim 22, wherein the transmitter is mounted on an imaging transducer of the imaging module.

27. The method of claim 22, wherein the one or more position sensors are mounted on an ultrasound treatment transducer of the therapy module.

28. The method of claim 22, wherein the transmitter is mounted on an ultrasound treatment transducer of the therapy module.

29. The method of claim 22, wherein delivering the therapy with the therapy module to the target tissue comprises delivering ultrasound for drug delivery to the target tissue.

* * * * *